United States Patent [19]
Eziri et al.

[11] Patent Number: 4,728,650
[45] Date of Patent: Mar. 1, 1988

[54] 3,4-DIHYDROBENZOPYRAN DERIVATIVES AND MEDICINAL USES THEREOF

[75] Inventors: Katsushi Eziri, Okayama; Koichi Kanehira, Kurashiki; Manzo Shiono, Kurashiki; Yoshiji Fujita, Kurashiki; Johji Yamahara, Otsu, all of Japan

[73] Assignee: Kuraray Co., Ltd., Kurashiki, Japan

[21] Appl. No.: 862,783

[22] Filed: May 13, 1986

[30] Foreign Application Priority Data

| May 13, 1985 [JP] | Japan | 60-102421 |
| Jun. 5, 1985 [JP] | Japan | 60-123394 |
| Jun. 17, 1985 [JP] | Japan | 60-132548 |

[51] Int. Cl.$^4$ .................. A61K 31/495; C07D 405/08
[52] U.S. Cl. .................................... 514/253; 514/456; 544/364; 544/376; 549/405; 549/407
[58] Field of Search ................. 544/364, 376; 514/253

[56] References Cited

U.S. PATENT DOCUMENTS

| 3,330,838 | 7/1967 | Augstein et al. ............ 549/407 |
| 4,221,793 | 9/1980 | Weber et al. ............... 544/376 |
| 4,321,270 | 3/1982 | Sundeen ..................... 544/376 |
| 4,374,990 | 2/1983 | Weber et al. ............... 544/360 |

*Primary Examiner*—Glennon H. Hollrah
*Assistant Examiner*—James H. Turnipseed
*Attorney, Agent, or Firm*—Burns, Doane, Swecker & Mathis

[57] ABSTRACT

There are provided novel 3,4-dihydrobenzopyran derivatives having anti-peptic ulcer, antitussive and/or expectorant activity. Also provided are medicinal uses of said 3,4-dihydrobenzopyran derivatives.

35 Claims, No Drawings

3,4-DIHYDROBENZOPYRAN DERIVATIVES AND MEDICINAL USES THEREOF

BACKGROUND OF THE INVENTION

1. Field of the Invention

The present invention relates to novel compounds having a chroman skeleton and medicinal use of said compounds as anti-peptic ulcer, antitussive and/or expectorant drugs.

2. Description of Prior Arts

Some of compounds having a chroman skeleton have heretofore been found to have several pharmacological actions. By way of illustration, 2,2,5,7,8-pentamethyl-6-(2-guanidinoethoxy)chroman has an antihypertensive action [Cesk. Farm. 29, 5, p. 125 (1980)] and 2-(N,N-dimethylamino)ethyl 2-(2,2,5,7,8-pentamethyl-6-chromanyloxy)isobutyrate, 2-(2,2,5,7,8-pentamethyl-6-chromanyloxy)isobutyl nicotinate, etc. have an anticholesteremic action [Japanese Kokai Tokkyo Koho No. 55-94382]. Moreover, vitamin E which also has a chroman skeleton is known to be involved in various physiological events in vivo.

While peptic ulcer is caused by various etiologic factors, it has been thought that peptic ulcer generally occurs as the result of an imbalance between the offensive factors such as acid, pepsin, gastric juice, etc. which are brought by hyperacidity, stress, inhibition of gastric blood circulation, drugs and other causes and the defensive factors associated with defensive strength which the digestive tract mucosa has in itself and so on. Heretofore, as agents adapted to attenuate the offensive factors, drugs having antacid, anticholinergic, antipepsin or antigastrin activity have been used clinically, while as agents adapted to potentiate the defensive factors, drugs having mucosal tissue repairing activity, mucosal tissue stimulating activity, mucosal fluid increasing activity and/or granulating activity have been utilized. As anti-peptic ulcer agents, a number of compounds such as cimetidine [N''-cyano-N-methyl-N'-[2-[(5-methyl-1H-imidazol-4-yl)methylthio]ethyl]guanidine] and sofalcone [2'-carboxymethoxy-4,4'-bis(3-methyl-2-butenyloxy)calcon] and teprenone [a 3:2 mixture of 5E-isomer and 5Z-isomer of (9E,13E)-6,10,14,18-tetramethyl-5,9,13,17-nonadecatetraen-3-one] are currently used in clinical practice. However, none of the compounds heretofore used as anti-peptic ulcer agents have a chroman skeleton.

Furthermore, among the hitherto-known anti-peptic ulcer agents, there are few drugs that have both the property to attenuate the offensive factors and the property to potentiate the defensive factors. Furthermore, many of the drugs capable of attenuating the offensive factors have side effects. For example, anticholinergic agents having parasympathetic nerve blocking activity tend to cause an excessive inhibition of gastric juice secretion to thereby suppress the activity of the stomach and decrease its digestive function, while antacids which neutralize the gastric acid transiently tend to cause an increased gastric acid secretion as a reaction.

Thus, although a large number of drugs have been used clinically as anti-peptic ulcer agents, the current situation calls for the development of an anti-peptic ulcer agent that will be more efficacious than these anti-peptic ulcer agents in clinical use, have both the property to attenuate the offensive factors and the property to potentiate the defensive factors, and be less toxic and as much free of side effects as possible to permit long-term repeated administration.

As regards antitussives or expectorants, too, a large number of drugs inclusive of eprazinone hydrochloride [3-[4-($\beta$-ethoxyphenethyl)-1-piperadinyl]-2-methyl-propiophenone hydrochloride] have been developed and put to clinical use. However, none of the known drugs in this field have a chroman skeleton.

The standing situation in this field is similar to that in the field of anti-peptic ulcer agents in that the development of antitussives and expectorants having low toxicity and few side effects that will permit long-term repeated administration has been required.

It is an object of the present invention to provide novel chroman compounds having useful pharmacological actions.

It is another object of the present invention to provide novel chroman compounds having high inhibitory activity against peptic ulcer and high safety.

It is a further object of the present invention to provide novel chroman compounds having high antitussive activity and high safety.

It is still another object of the present invention to provide novel chroman compounds having high expectorant activity and high safety.

It is a further yet object of the present invention to provide medicinal uses for said novel chroman compounds in connection with the application thereof as anti-peptic ulcer, antitussive and/or expectorant drugs.

These objects as well as other objects and advantages of the present invention will become apparent to those skilled in the art from the following detailed description.

SUMMARY OF THE INVENTION

The present invention provides a 3,4-dihydrobenzopyran derivative of general formula

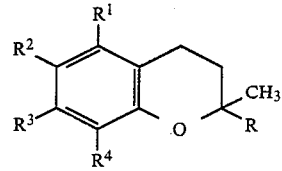

(I)

wherein $R^1$ and $R^4$ each means a hydrogen atom or a lower alkyl group; $R^2$ means a hydrogen atom, a halogen atom, a lower alkoxyl group or a lower alkenyloxy group; $R^3$ means a hydrogen atom, a lower alkyl group or a lower alkoxyl group; R means a group of the following formula (1) or a group of the following formula (2)

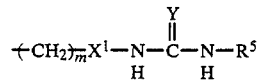

(1)

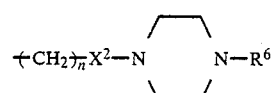

(2)

wherein $R^5$ means a hydrogen atom or a lower alkyl group; $X^1$ means a methylene group or a carbonyl group; Y means a sulfur atom or an imino group; m means an integer of 0, 1 or 2, n means an integer of 0, 1 or 2; $X^2$ means a methylene group or a carbonyl group; $R^6$ when $X^2$ means a methylene group means a lower alkyl group optionally substituted by a hydroxyl group,

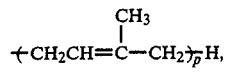

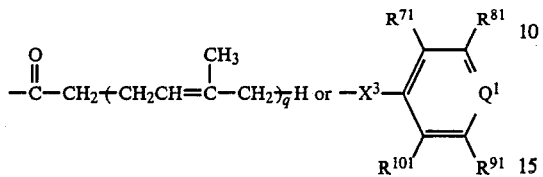

and when $X^2$ means a carbonyl group means

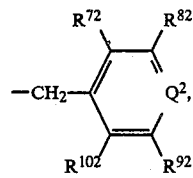

where p and q each means an integer of 0 to 4; $X^3$ means a methylene group or a carbonyl group; $Q^1$ means a nitrogen atom (=N—) or an optionally substituted carbon atom

where $R^{111}$ means a hydrogen atom, a lower alkoxyl group, a halogen atom, a di-lower alkylamino group or a nitro group; $R^{71}$, $R^{81}$, $R^{91}$ and $R^{101}$ each means a hydrogen atom or a lower alkoxyl group; $Q^2$ means a nitrogen atom (=N—) or an optionally substituted carbon atom

where $R^{112}$ means a hydrogen atom, a lower alkoxyl group, a halogen atom, a di-lower alkylamino group or a nitro group; and $R^{72}$, $R^{82}$, $R^{92}$ and $R^{102}$ each means a hydrogen atom or a lower alkoxyl group; or a pharmacologically acceptable salt thereof [In the following description, said 3,4-dihydrobenzopyran derivative and salt thereof are collectively referred to as the 3,4-dihydrobenzopyran compound [I].]

In another aspect, the present invention provides drugs and pharmaceutical compositions containing said 3,4-dihydrobenzopyran compound [I] as an active ingredient.

DETAILED DESCRIPTION OF THE INVENTION

Referring to the above general formula (I), the lower alkyl group designated by $R^1$, $R^3$, $R^4$, $R^5$ and $R^6$ may for example be methyl, ethyl, propyl, butyl, isopentyl, etc. and the lower alkyl group substituted by a hydroxyl group designated by $R^6$ may for example be 2-hydroxyethyl, 3-hydroxypropyl, etc. The lower alkoxyl group designated by $R^2$, $R^3$, $R^{71}$, $R^{81}$, $R^{91}$, $R^{101}$, $R^{111}$, $R^{72}$, $R^{82}$, $R^{92}$, $R^{102}$ and $R^{112}$ may for example be methoxy, ethoxy, propoxy, butoxy, etc. The lower alkenyloxy group designated by $R^2$ may for example be allyloxy, prenyloxy, geranyloxy, etc.; the halogen atom designated by $R^2$, $R^{111}$ and $R^{112}$ may be fluorine, chlorine, bromine or iodine; and the di-lower alkylamino group designated by $R^{111}$ and $R^{112}$ may for example be dimethylamino, diethylamino, dipropylamino, ethylmethylamino, etc.

According to the substituent group R, 3,4-dihydrobenzopyran derivatives of general formula (I) may be classified into the following two types.

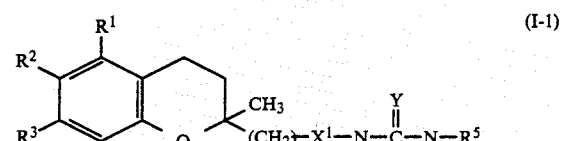

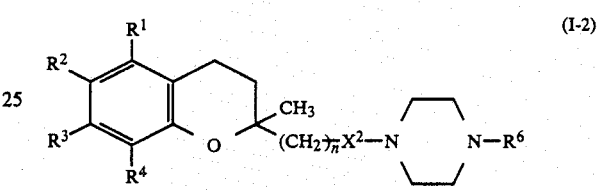

wherein $R^1$, $R^2$, $R^3$, $R^4$, $R^5$, $R^6$, $X^1$, $X^2$, Y, m and n have the same meanings as defined hereinbefore.

The following is a partial listing of 3,4-dihydrobenzopyran derivatives of general formula (I).

N-(3,4-Dihydro-6-methoxy-2,5,7,8-tetramethyl-2H-benzopyran-2-yl)acetylguanidine [Compound (1)]

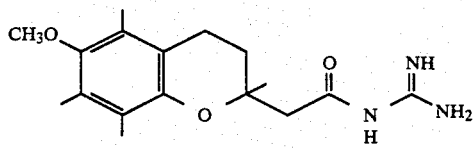

N-(3,4-Dihydro-6-ethoxy-2,5,7,8-tetramethyl-2H-benzopyran-2-yl)acetylguanidine [Compound (2)]

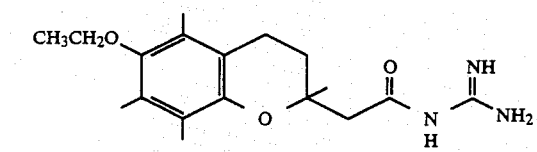

N-(3,4-Dihydro-6-prenyloxy-2,5,7,8-tetramethyl-2H-benzopyran-2-yl)acetylguanidine [Compound (3)]

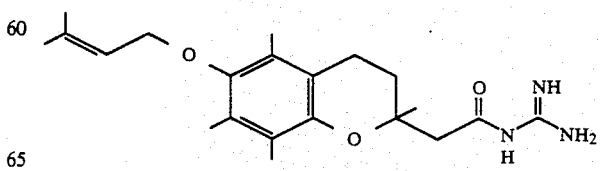

N-(3,4-Dihydro-6-methoxy-2,5,7,8-tetramethyl-2H-benzopyran-2-yl)carbonylguanidine [Compound (4)]

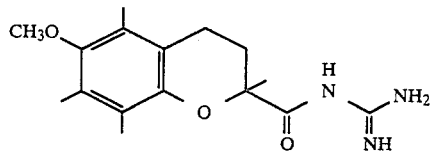

N-[2-(3,4-Dihydro-6-methoxy-2,5,7,8-tetramethyl-2H-benzopyran-2-yl)propionyl]guanidine [Compound (5)]

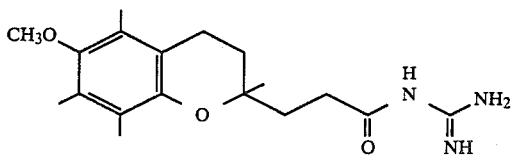

N-(3,4-Dihydro-6-methoxy-2-methyl-2H-benzopyran-2-yl)acetylguanidine [Compound (6)]

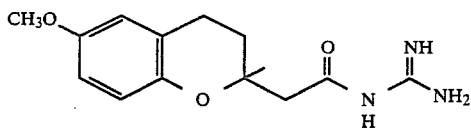

N-(3,4-Dihydro-7-methoxy-2-methyl-2H-benzopyran-2-yl)acetylguanidine [Compound (7)]

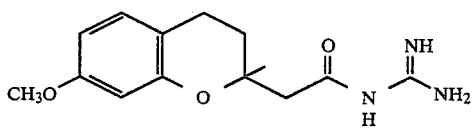

N-(3,4-Dihydro-6-chloro-2-methyl-2H-benzopyran-2-yl)acetylguanidine [Compound (8)]

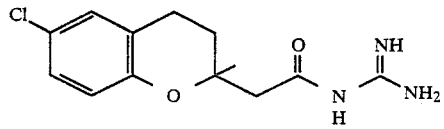

N-[2-(3,4-Dihydro-6-methoxy-2,5,7,8-tetramethyl-2H-benzopyran-2-yl)ethyl]-N'-methylthiourea [Compound (9)]

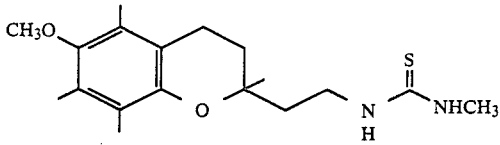

N-[2-(3,4-Dihydro-6-methoxy-2,5,7,8-tetramethyl-2H-benzopyran-2-yl)ethyl]guanidine [Compound (10)]

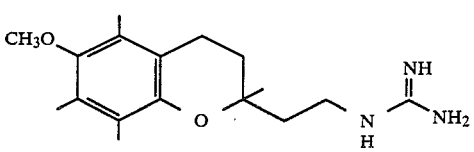

N-[2-(3,4-Dihydro-6-methoxy-2,5,7,8-tetramethyl-2H-benzopyran-2-yl)ethyl]-N'-methylguanidine [Compound (11)]

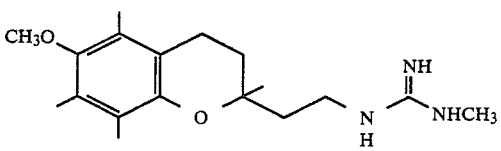

3,4-Dihydro-6-methoxy-2-[2-(piperazin-1-yl)ethyl]-2,5,7,8-tetramethyl-2H-benzopyran [Compound (12)]

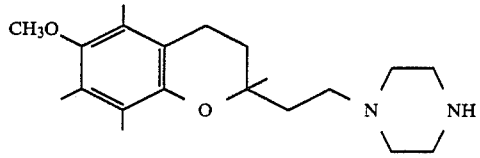

3,4-Dihydro-6-methoxy-2-[2-[4-(3-methyl-2-butenyl)-piperazin-1-yl]ethyl]-2,5,7,8-tetramethyl-2H-benzopyran [Compound (13)]

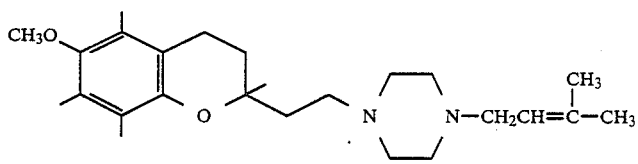

3,4-Dihydro-6-methoxy-2-[2-[4-(3,7-dimethyl-2,6-octadienyl)piperazin-1-yl]ethyl]-2,5,7,8-tetramethyl-2H-benzopyran [Compound (14)]

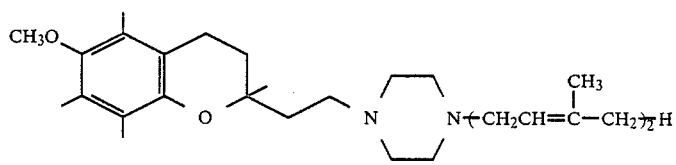

3,4-Dihydro-6-methoxy-2-[2-[4-(3,7,11-trimethyl-2,6,10-dodecatrienyl)piperazin-1-yl]ethyl]-2,5,7,8-tetramethyl-2H-benzopyran [Compound (15)]

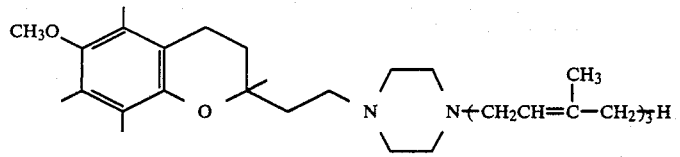

3,4-Dihydro-6-methoxy-2-[2-[4-(3,7,11,15-tetramethyl-2,6,10,14-hexadecatetraenyl)piperazin-1-yl]ethyl]-2,5,7,8-tetramethyl-2H-benzopyran [Compound (16)]

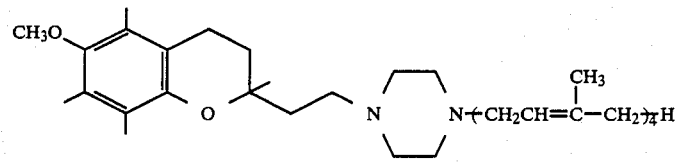

3,4-Dihydro-6-methoxy-2-[2-[4-(3,4,5-trimethoxybenzoyl)piperazin-1-yl]ethyl]-2,5,7,8-tetramethyl-2H-benzopyran [Compound (17)]

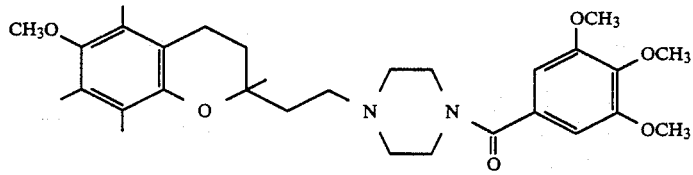

3,4-Dihydro-6-methoxy-2-[2-[4-(3,4,5-trimethoxybenzyl)piperazin-1-yl]ethyl]-2,5,7,8-tetramethyl-2H-benzopyran [Compound (18)]

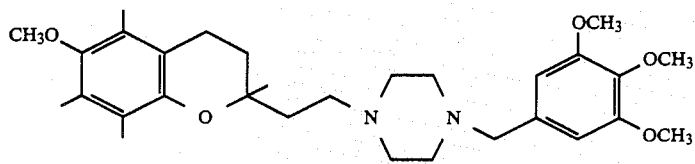

1-[2-(3,4-Dihydro-6-methoxy-2,5,7,8-tetramethyl-2H-benzopyran-2-yl)ethyl]-4-(4-methoxybenzoyl)piperazine [Compound (19)]

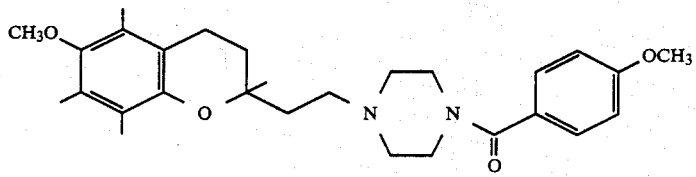

1-[2-(3,4-Dihydro-6-methoxy-2,5,7,8-tetramethyl-2H-benzopyran-2-yl)ethyl]-4-(4-dimethylaminobenzoyl)piperazine [Compound (20)]

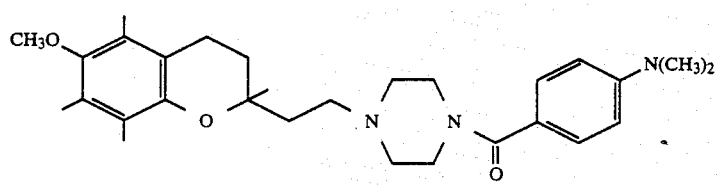

1-[2-(3,4-Dihydro-6-methoxy-2,5,7,8-tetramethyl-2H-benzopyran-2-yl)ethyl]-4-(4-nitrobenzoyl)piperazine [Compound (21)]

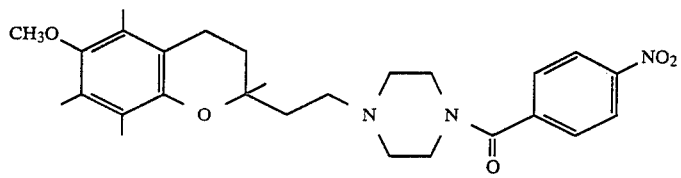

1-[2-(3,4-Dihydro-6-methoxy-2,5,7,8-tetramethyl-2H-benzopyran-2-yl)ethyl]-4-(4-bromobenzoyl)piperazine [Compound (22)]

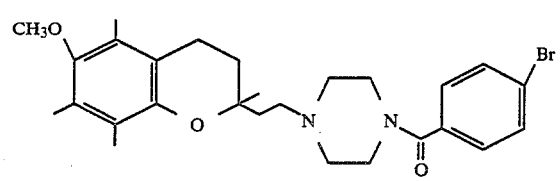

1-[2-(3,4-Dihydro-6-methoxy-2,5,7,8-tetramethyl-2H-benzopyran-2-yl)ethyl]-4-(4-pyridylcarbonyl)piperazine [Compound (23)]

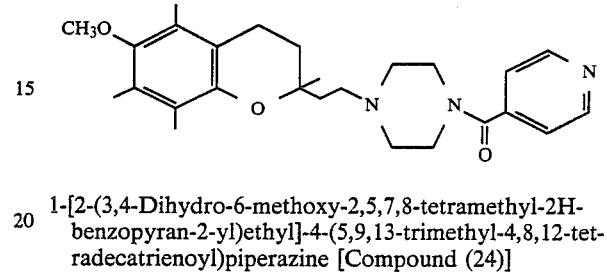

1-[2-(3,4-Dihydro-6-methoxy-2,5,7,8-tetramethyl-2H-benzopyran-2-yl)ethyl]-4-(5,9,13-trimethyl-4,8,12-tetradecatrienoyl)piperazine [Compound (24)]

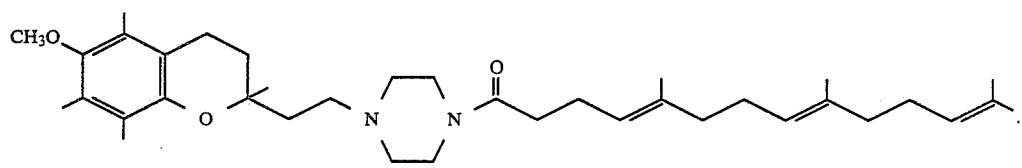

1-[2-(3,4-Dihydro-7-methoxy-2-methyl-2H-benzopyran-2-yl)ethyl]-4-(3,4,5-trimethoxybenzoyl)piperazine [Compound (25)]

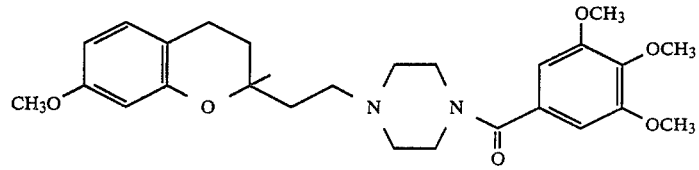

1-[2-(6-Chloro-3,4-dihydro-2-methyl-2H-benzopyran-2-yl)ethyl]-4-(4-methoxybenzoyl)piperazine [Compound (26)]

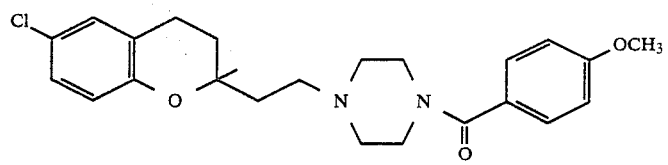

1-[3-(3,4-Dihydro-6-methoxy-2,5,7,8-tetramethyl-2H-benzopyran-2-yl)propyl]-4-(4-methoxybenzoyl)piperazine [Compound (27)]

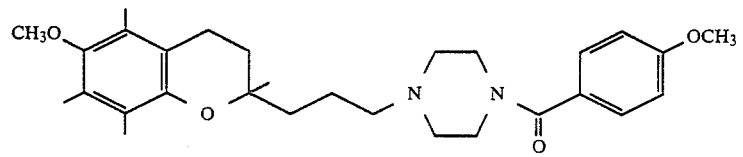

1-[(3,4-Dihydro-6-methoxy-2,5,7,8-tetramethyl-2H-benzopyran-2-yl)acetyl]-4-(2,3,4-trimethoxybenzyl)piperazine [Compound (28)]

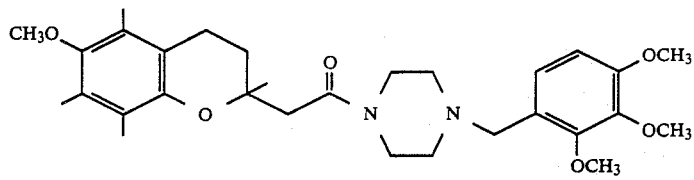

1-[(6-Chloro-3,4-dihydro-2-methyl-2H-benzopyran-2-yl)acetyl]-4-(2,3,4-trimethoxybenzyl)piperazine [Compound (29)]

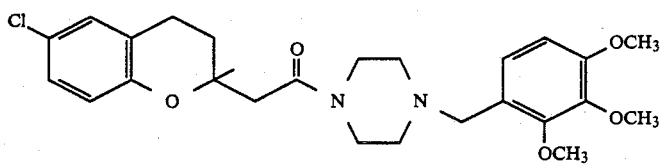

1-[(3,4-Dihydro-6-methoxy-2,5,7,8-tetramethyl-2H-benzopyran-2-yl)carbonyl]-4-(2,3,4-trimethoxybenzyl)piperazine [Compound (30)]

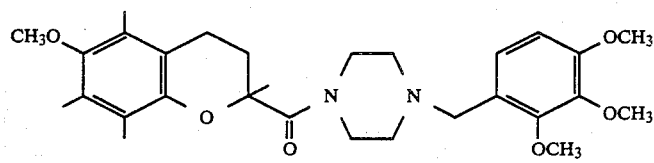

1-[2-(3,4-Dihydro-6-methoxy-2,5,7,8-tetramethyl-2H-benzopyran-2-yl)ethyl]-4-(2,3,4-trimethoxybenzyl)piperazine [Compound (31)]

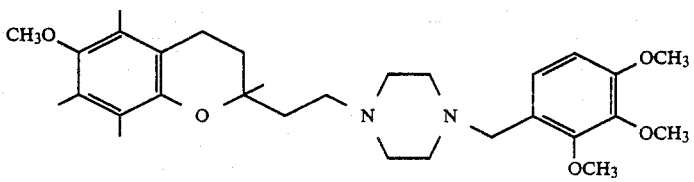

1-Benzoyl-4-[2-(3,4-dihydro-6-methoxy-2,5,7,8-tetramethyl-2H-benzopyran-2-yl)ethyl]piperazine [Compound (32)]

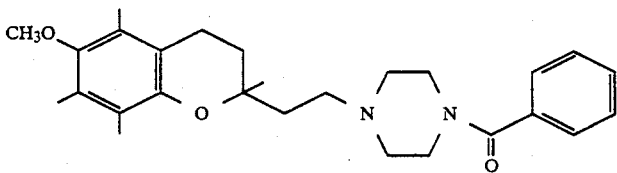

1-[2-(3,4-Dihydro-6-methoxy-2,5,7,8-tetramethyl-2H-benzopyran-2-yl)ethyl]-4-methylpiperazine [Compound (33)]

1-[2-(3,4-Dihydro-6-methoxy-2,5,7,8-tetramethyl-2H-benzopyran-2-yl)ethyl]-4-isopentylpiperazine [Compound (34)]

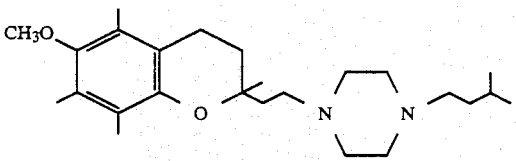

1-[2-(3,4-Dihydro-6-methoxy-2,5,7,8-tetramethyl-2H-benzopyran-2-yl)ethyl]-4-(2-hydroxyethyl)piperazine [Compound (35)]

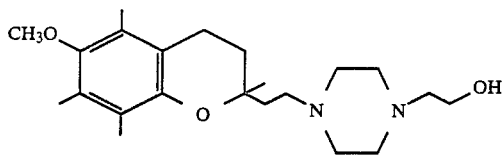

1-[2-(3,4-Dihydro-6-methoxy-2,5,7,8-tetramethyl-2H-benzopyran-2-yl)ethyl]-4-(3-hydroxypropyl)piperazine [Compound (36)]

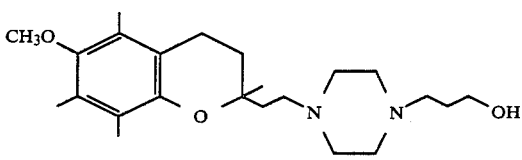

Examples of the pharmacologically acceptable salts of the 3,4-dihydrobenzopyran derivatives of general formula (I) include salts with mineral acids such as hydrochloric acid, sulfuric acid, etc., salts with organic sulfonic acids such as methanesulfonic acid, p-toluenesulfonic acid, etc., and salts with organic carboxylic acids such as acetic acid, propionic acid, succinic acid, lactic acid, tartaric acid, malic acid, citric acid and so on.

The 3,4-dihydrobenzopyran derivatives of general formula (I-1) wherein $X^1$ means a carbonyl group can be produced by various methods inclusive of the following.

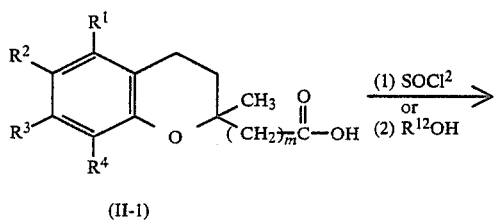

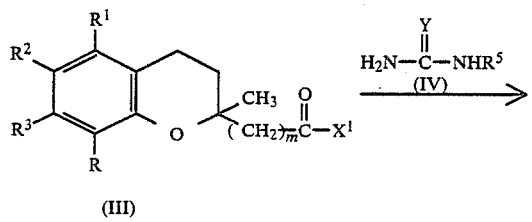

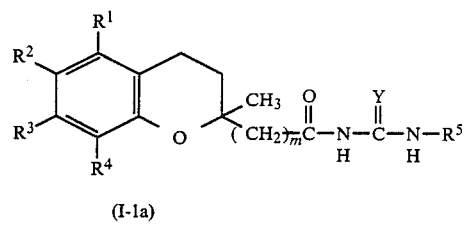

(I-1a)

In the above formulas, $R^1$, $R^2$, $R^3$, $R^4$, $R^5$, Y and m have the same meanings as defined hereinbefore; $R^{12}$ means a lower alkyl group; and $Z^1$ means a chlorine atom or a lower alkoxyl group.

Thus, a known carboxylic acid of general formula (II-1) is treated with an equimolar or solvent amount of thionyl chloride, in the presence or absence of an inert solvent such as methylene chloride, dichloroethane, benzene, etc. at a temperature of room temperature to reflux temperature to give an acid chloride of general formula (III). The formation of acid chloride can be accelerated by adding a catalytic amount of pyridine, dimethylformamide or the like to the above reaction system. From the above reaction mixture containing the product acid chloride of general formula (III), the unreacted thionyl chloride, solvent and other low-boiling substances are removed by distillation under reduced pressure and the residue is diluted with a solvent such as methylene chloride, dichloroethane, benzene, dioxane, tetrahydrofuran, etc. The dilution thus prepared is added dropwise to an equimolar (relative to acid chloride) or solvent amount of a guanidine or thiourea derivative of general formula (IV) dissolved in a solvent mixture of alcohol and either dioxane or tetrahydrofuran at a temperature of about $-20°$ C. to $10°$ C. and the mixture is further stirred at room temperature to give a 3,4-dihydrobenzopyran derivative of general formula (I-1a). Such 3,4-dihydrobenzopyran derivative of general formula (I-1a) may be produced as follows. Thus, a carboxylic acid of general formula (II-1) is made into a lower alkyl ester in the conventional manner and this ester is reacted with an equimolar or solvent amount of a guanidine or thiourea derivative of general formula (IV) in the presence or absence of an inert solvent such as methanol, ethanol, tetrahydrofuran, etc. at a temperature of room temperature to about $100°$ C. The separation and purification of the 3,4-dihydrobenzopyran derivative (I-1a) from the reaction mixture can be performed in the conventional manner.

The 3,4-dihydrobenzopyran derivatives of general formula (I-1) wherein X is a methylene group can be produced by the following and other methods.

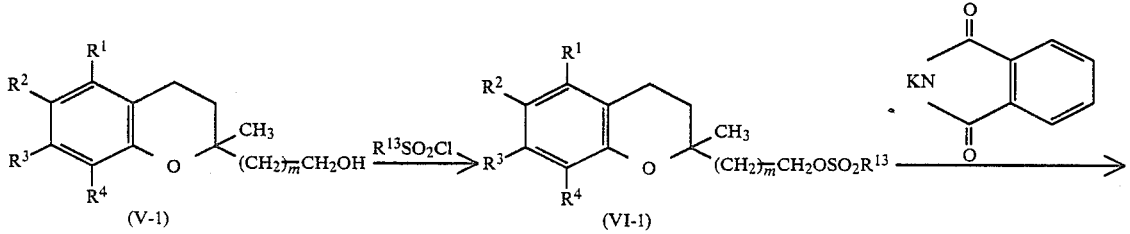

-continued

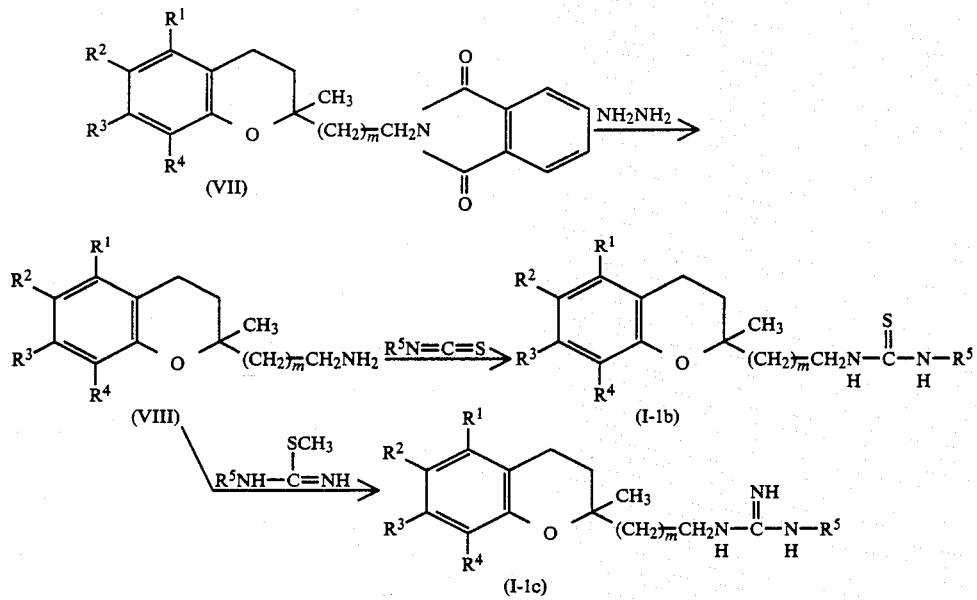

wherein $R^1$, $R^2$, $R^3$, $R^4$, $R^5$ and m have the same meanings as defined hereinbefore; and $R^{13}$ means a methyl group, a phenyl group or a p-tolyl group.

Thus, a known alcohol of general formula (V-1) is reacted with an organic sulfonyl chloride in the presence of pyridine in the conventional manner to give a sulfonic acid ester of general formula (VI-1) and this sulfonic acid ester is then reacted with potassium phthalimide to give an N-substituted phthalimide of general formula (VII), which is further treated with hydrazine to give an amine of general formula (VIII).

This amine of general formula (VIII) is reacted with 0.9 to 1.1 molar equivalents of an isothiocyanate in an inert solvent such as methylene chloride, dichloroethane, benzene, methanol, etc. at a temperature of room temperature to reflux temperature to give a 3,4-dihydrobenzopyran derivative of general formula (I-1b). And the amine of general formula (VIII) is reacted with 0.9 to 1.2 molar equivalents of methylisothiourea in an inert solvent such as methanol, ethanol, etc. at a temperature of room temperature to reflux temperature to give a 3,4-dihydrobenzopyran derivative of general formula (I-1c). The separation and purification of 3,4-dihydrobenzopyran derivative (I-1b) or 3,4-dihydrobenzopyran derivative (I-1c) from the reaction mixture can be carried out in the conventional manner.

Referring to 3,4-dihydrobenzopyran derivatives having the general formula (I-2), the 3,4-dihydrobenzopyran derivatives of general formula (I-2) wherein $X^2$ is a carbonyl group can be produced by the following and other methods.

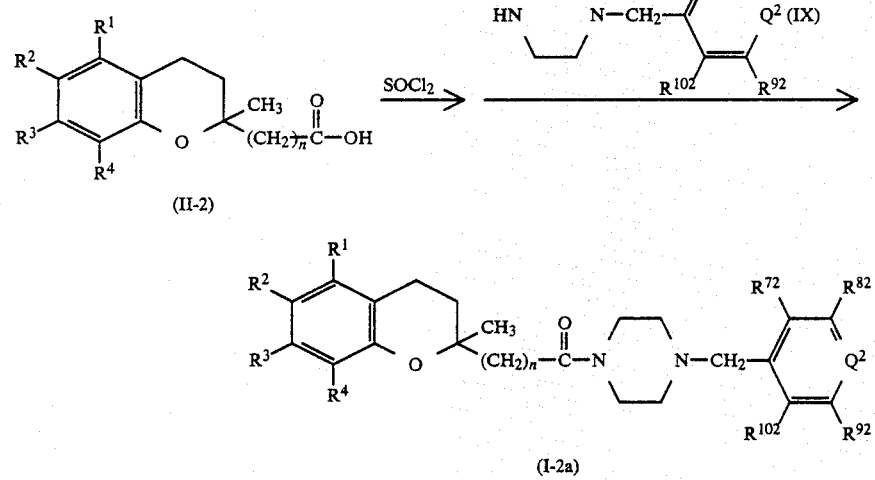

In the above formulas, $R^1$, $R^2$, $R^3$, $R^4$, $R^{72}$, $R^{82}$, $R^{92}$, $R^{102}$, $Q^2$ and n have the same meanings as defined hereinbefore.

Thus, a known carboxylic acid of general formula (II-2) is reacted with an equimolar or solvent amount of thionyl chloride in the presence or absence of an inert solvent such as methylene chloride, dichloroethane, benzene, etc. at a temperature of room temperature to reflux temperature to give the corresponding acid chloride. This formation of acid chloride may be accelerated by adding a catalytic amount of pyridine, dimethylformamide or the like to the above reaction system. From the reaction mixture containing the product acid chloride, the unreacted thionyl chloride, solvent and other low-boiling substances are distilled off under reduced pressure and the residue is diluted with a solvent such as methylene chloride, dichloroethane, benzene, toluene, diethyl ether, etc. This dilution is then reacted with about 1 to 2 molar equivalents of a 4-substituted piperazine of general formula (IX) in the presence of about 1 to 5 molar equivalents of an organic tertiary amine such as triethylamine, tributylamine, etc. at a temperature of about $-20°$ C. to $50°$ C., preferably $0°$ C. to room temperature, to give a 3,4-dihydrobenzopyran derivative of general formula (I-2a). The separation and purification of the 3,4-dihydrobenzopyran derivative of general formula (I-2a) from the reaction mixture can be carried out in the conventional manner.

The 3,4-dihydrobenzopyran derivatives of general formula (I-2) wherein $X^2$ is a methylene group can be produced by the following and other methods.

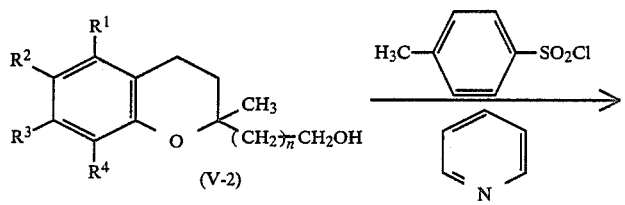

(V-2)

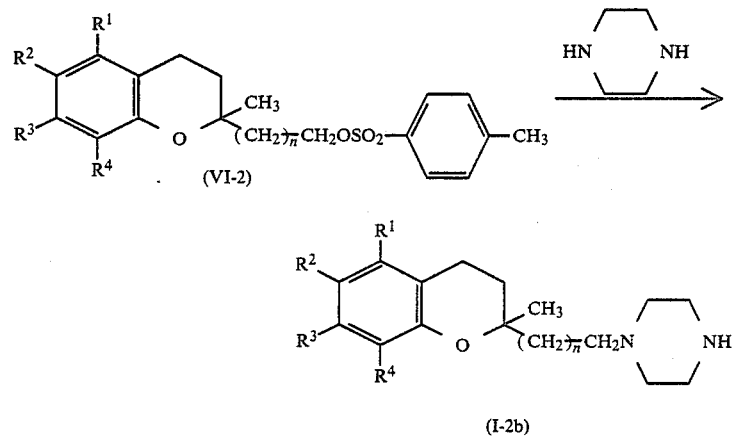

(VI-2)

(I-2b)

[Method (i)]

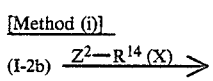

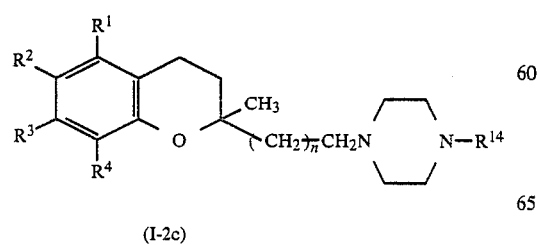

(I-2c)

[Method (ii)]

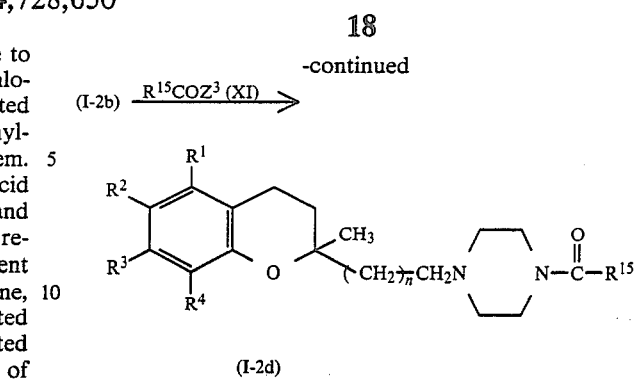

(I-2d)

[Method (iii)]

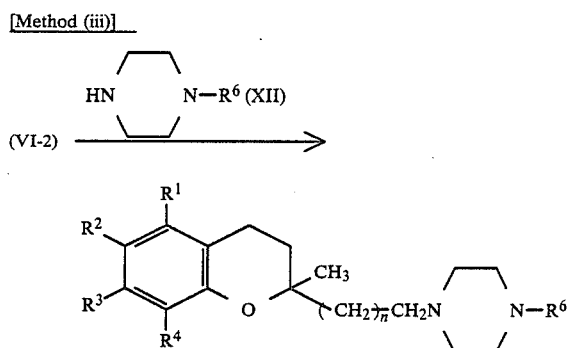

(I-2e)

In the above formulas, $R^1$, $R^2$, $R^3$, $R^4$, $R^6$ and n have the same meanings as defined hereinbefore; $R^{14}$ means $R^{15}$ means

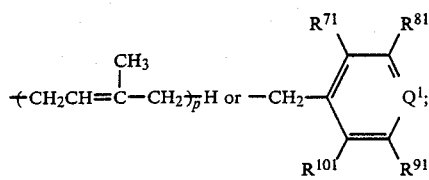

or

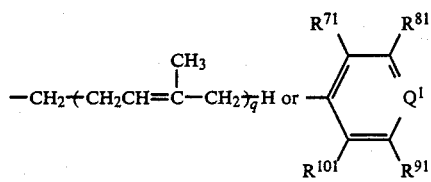

wherein $R^{71}$, $R^{81}$, $R^{91}$ $R^{101}$, $Q^1$, p and q have the same meanings as defined hereinbefore; $Z^2$ means a halogen atom, an organic sulfonyloxy group or a group of the formula $-(OSO_2O)_{\overline{\pi}}$. and $Z^3$ means a halogen atom.

Thus, in the conventional manner, a known alcohol of general formula (V-2) is reacted with 1.0 to 1.2 molar equivalents of p-toluenesulfonyl chloride in the presence of an organic tertiary amine such as pyridine, triethylamine, etc. to give the corresponding p-toluenesulfonic acid ester of general formula (VI-2). This p-toluenesulfonic acid ester is then reacted with 1.0 to 10.0 molar equivalents of piperazine at a temperature of 60° C. to 130° C. to give a 3,4-dihydrobenzopyran derivative of general formula (I-2b).

Method (i)

The 3,4-dihydrobenzopyran derivative (I-2b) prepared by the above procedure is reacted with 1.0 to 1.1 molar equivalents of a base such as an organolithium compound, e.g. butyllithium, methyllithium, phenyllithium, etc., in an inert solvent such as tetrahydrofuran or 1,2-dimethoxyethane at a temperature of −78° C. to room temperature and, further, with 1.0 to 1.2 molar equivalents of an organic halide, organic sulfonic acid ester or organic sulfuric acid ester of general formula (X) at a temperature of −78° C. to room temperature. The above procedure gives a 3,4-dihydrobenzopyran derivative of general formula (I-2c).

Method (ii)

The 3,4-dihydrobenzopyran derivative (I-2b) prepared by the procedure described hereinbefore is reacted with 1.0 to 2.0 molar equivalents of a carboxylic acid halide of general formula (XI) in an inert solvent such as tetrahydrofuran, 1,2-dimethoxyethane, dichloromethane, 1,2-dichloroethane, benzene, toluene, etc. in the presence of an equimolar or solvent amount of a base such as an organic tertiary amine, e.g. pyridine, triethylamine, etc. at a temperature of about −20° C. to 50° C. to give a 3,4-dihydrobenzopyran derivative of general formula (I-2d).

Method (iii)

The p-toluenesulfonic acid ester (VI-2) prepared by the procedure described hereinbefore is reacted with 1.0 to 5.0 molar equivalents of a piperazine derivative of general formula (XII) at a temperature of 60° C. to 130° C. to give a 3,4-dihydrobenzopyran derivative of general formula (I-2e).

The separation and purification of p-toluenesulfonic acid ester (VI-2), 3,4-dihydrobenzopyran derivative (I-2b), 3,4-dihydrobenzopyran derivative (I-2c), 3,4-dihydrobenzopyran derivative (I-2d) and 3,4-dihydrobenzopyran derivative (I-2e) from the respective reaction mixtures can be carried out in the conventional manner.

The pharmacologically acceptable salts of 3,4-dihydrobenzopyran derivatives of general formula (I) can be produced by reacting each 3,4-dihydrobenzopyran derivative with about 0.9 to 1.1 molar equivalents of the corresponding acid in an inert solvent such as tetrahydrofuran, diethyl ether, methanol, ethanol, acetone, etc. at a temperature of about −20° C. to about 50° C. The separation and purification of the pharmacologically acceptable salts of 3,4-dihydrobenzopyran derivatives (I) from the above reaction mixtures can be carried out in accordance with the procedures well-known to those skilled in the art for the separation and purification of salts.

The comparative studies conducted on the relative anti-peptic ulcer action of the 3,4-dihydrobenzopyran compound [I] of the present invention and some control drugs including cimetidine, sofalcone, teprenone, etc. and the results of the studies are described below.

1. Stress ulcer

Method

Male mice of ddK strain (body weights, 18–20 g) were placed in a stress cage in groups of 6 animals and immersed down to the level of the xiphoid process in a water bath at 22±1° C. to give a stress. Five hours later the mice were raised from the water bath and the stomach was removed under ether anesthesia. Into the stomach was infused 1.2 ml of a 10% aqueous solution of formaldehyde and, then, the stomach was immersed in a 10% aqueous solution of formaldehyde for 10 minutes for fixation of the tissue. After fixation, an incision was made along the greater curvature for observing ulcers which had appeared in the glandular portion of the stomach. The degree of ulceration was classified according to the following ulcer index scale and the % inhibition of ulcer was estimated.

Ulcer index
 0: No ulcer
 1: Slight hemorrhage
 2: Hemorrhage and erosion
 3: Severe hemorrhage and erosion Each test compound was orally administered, as suspended in a gum arabic solution in concentration of 5%, to mice 10 minutes before stress loading.

Results

For comparative purposes, the doses of test compounds and the ulcer indices for treated and untreated mice are shown in Table 1. The % inhibitions of ulcer by the test compounds are also shown.

TABLE 1

| Test compound | Dose (mg/kg, p.o.) | Ulcer index (mm) (mean ± S.E.) | % Inhibition |
|---|---|---|---|
| Control (untreated) | — | 2.63 ± 0.18 | — |
| Atropine sulfate | 30 | 0.50 ± 0.29** | 80.99 |
| Cimetidine | 200 | 1.33 ± 0.21** | 49.43 |
| Guanethidine sulfate | 100 | 2.00 ± 0.26 | 23.95 |

TABLE 1-continued

| Test compound | Dose (mg/kg, p.o.) | Ulcer index (mm) (mean ± S.E.) | % Inhibition |
|---|---|---|---|
| Compound (1) | 25 | 1.00 ± 0.63** | 61.98 |

Note
**Significantly different from the control group (p < 0.01, t-test)

2. Pyloric ligation-induced ulcer (Shay ulcer)

Method

Male Wistar rats (body weights, 180-200 g) were used in groups of 7 animals. After 48-hour fasting, laparotomy was performed under ether anesthesia and the pylorus was ligated with a suture. After 13 hours, the stomach was isolated under ether anesthesia and gastric juice was collected. The gastric juice was centrifuged at 3,000 r.p.m. for 10 minutes and the volume and pH value of gastric juice were determined. The pH value was determined by using pH paper. After collection of gastric juice, a 10% aqueous solution of formaldehyde was infused into the stomach until the stomach was inflated. Then, the stomach was immersed in a 10% aqueous solution of formaldehyde for 10 minutes for fixation of the tissue. After fixation, an incision was made along the greater curvature for observing ulcers which had developed in the glandular portion of the stomach. The degree of ulcer was classified according to the following ulcer index scale.

Ulcer index
 0: No ulcer
 1: Bleeding spots
 2: 1-5 small ulcers (<3 mm in diameter)
 3: Six or more small ulcers or one large ulcer (>3 mm in diameter)
 4: Two or more large ulcers
 5: Perforating ulcer Each test compound was administered, as suspended in a gum arabic solution in concentration of 5%, into the duodenum immediately after pyloric ligation.

Results

The doses of each test compound and the volumes and pH values of gastric juice and the ulcer indices for treated and untreated rats are shown in Table 2.

TABLE 2

| Test compound | Dose (mg/kg, i.d.) | Volume of gastric juice (ml/100 g body weight) | pH value of gastric juice | Ulcer index (mean ± S.E.) |
|---|---|---|---|---|
| Control (untreated) | — | 5.09 ± 0.40 | 1.77 ± 0.54 | 3.86 ± 0.40 |
| Cimetidine | 200 | 5.13 ± 0.99 | 2.29 ± 0.88 | 1.71 ± 0.18** |
| Compound (1) | 50 | 3.36 ± 0.90 | 2.07 ± 0.94 | 2.33 ± 0.42* |

(Note)
*Significantly different from the control group (p < 0.05, t-test)
**Significantly different from the control group (p < 0.01, t-test)

3. Indomethacin-induced ulcer

Method

Male Wistar rats (body weights, 170-210 g) were used in groups of 6 to 8 animals. Indomethacin, 20 mg/kg body weight, was injected subcutaneously to rats which had been deprived of food for 24 hours. After 7 hours, the stomach was excised under ether anesthesia. A 10% aqueous solution of formaldehyde was infused into the stomach until the stomach was inflated and, then, the stomach was immersed in a 10% aqueous solution of formaldehyde for 10 minutes for fixation of the tissue. After fixation, an incision was made along the greater curvature and the length of ulcers occurring in the glandular portion of the stomach was measured. The total length of ulcers occurring in a rat was taken as an ulcer index. Each test compound was orally administered, as suspended in a gum arabic solution in concentration of 5%, to rats 10 minutes before subcutaneous injection of indomethacin.

Results

The doses of test compounds and the ulcer indices for treated and untreated rats are shown in Table 3 for purposes of comparison. The % inhibition of ulcer by each test compound as estimated from the ulcer index is also presented in the same table.

TABLE 3

| Test compound | Dose (mg/kg, p.o.) | Ulcer index (mm) (mean ± S.E.) | % Inhibition |
|---|---|---|---|
| Control (untreated) | — | 10.36 ± 2.07 | — |
| Cimetidine | 200 | 1.35 ± 0.48** | 86.97 |
| Compound (1) | 50 | 2.30 ± 0.58** | 77.80 |

Note
**Significantly different from the control group (p < 0.01, t-test)

4. Hydrochloric acid-ethanol-induced ulcer

Method

Male Wistar rats (body weights, 160-190 g) were used in groups of 6 to 8 animals. One milliliter of a 60% aqueous solution of ethanol containing 150 mM hydrochloric acid was administered orally to rats which had been deprived of food for 24 hours. After one hour, the stomach was excised under ether anesthesia. In a manner similar to that described in study for indomethacin-induced ulcer, the ulcer index was determined. Each test compound was orally administered, as suspended in a gum arabic solution in concentration of 5%, to rats 1 hour before administration of hydrochloric acid-ethanol.

Results

The doses of test compounds and ulcer indices for treated and untreated rats are shown in Tables 4, 5, 6, 8, 9, 10, 11 and 12 for comparison. The % inhibition of ulcer by each test compound as estimated on the basis of ulcer index is shown in Tables 7, 8, 9, 10, 11 and 12.

TABLE 4

| Test compound | Dose (mg/kg, p.o.) | Ulcer index (mm) (mean ± S.E.) |
|---|---|---|
| Control (untreated) | — | 7.36 ± 1.23 |
| Cimetidine | 200 | 1.63 ± 0.49** |
| Compound (1) | 50 | 0.39 ± 0.19** |

Note
**Significantly different from the control group (p < 0.01, t-test)

TABLE 5

| Test compound | Dose (mg/kg, p.o.) | Ulcer index (mm) (mean ± S.E.) |
|---|---|---|
| Control (untreated) | — | 11.09 ± 1.49 |
| Compound (7) | 12.5 | 3.12 ± 0.66** |

TABLE 5-continued

| Test compound | Dose (mg/kg, p.o.) | Ulcer index (mm) (mean ± S.E.) |
|---|---|---|
| Compound (2) | 25 | 0.50 ± 0.34** |
| Compound (3) | 25 | 0.14 ± 0.14** |
| Compound (5) | 25 | 0.00 ± 0.00** |
| Compound (9) | 25 | 5.84 ± 0.75* |
| Compound (10) | 50 | 3.04 ± 1.33** |
| Compound (11) | 50 | 0.20 ± 0.14** |

Note
*Significantly different from the control group (p < 0.05, t-test)
**Significantly different from the control group (p < 0.01, t-test)

TABLE 6

| Test compound | Dose (mg/kg, p.o.) | Ulcer index (mm) (mean ± S.E.) |
|---|---|---|
| Control (untreated) | — | 9.69 ± 1.68 |
| Compound (4) | 25 | 0.00 ± 0.00** |
| Compound (6) | 25 | 2.03 ± 1.04** |
| Compound (7) | 25 | 1.53 ± 0.66** |
| Compound (8) | 25 | 0.00 ± 0.00** |

Note
**Significantly different from the control group (p < 0.01, t-test)

TABLE 7

| Test compound | Dose (mg/kg, p.o.) | % Inhibition |
|---|---|---|
| Cimetidine | 200 | 77.9 |
| Sofalcone | 25 | 25.8 |
| " | 50 | 38.3 |
| Teprenone | 12.5 | 33.8 |
| " | 25 | 78.4 |
| Compound (7) | 12.5 | 71.9 |
| Compound (1) | 25 | 91.1 |
| Compound (2) | 25 | 89.0 |
| Compound (3) | 25 | 98.7 |
| Compound (4) | 25 | 100 |
| Compound (5) | 25 | 100 |
| Compound (6) | 25 | 79.1 |
| Compound (7) | 25 | 84.2 |
| Compound (8) | 25 | 100 |
| Compound (9) | 25 | 47.3 |
| Compound (9) | 50 | 95.4 |
| Compound (10) | 50 | 72.6 |
| Compound (11) | 50 | 98.2 |

TABLE 8

| Test compound | Dose (mg/kg, p.o.) | Ulcer index (mm) (mean ± S.E.) | % Inhibition |
|---|---|---|---|
| Control (untreated) | — | 9.69 ± 1.68 | — |
| Compound (12) | 50 | 0.00 ± 0.00** | 100 |
| Compound (12) | 25 | 0.13 ± 0.13** | 98.7 |
| Compound (13) | 50 | 0.00 ± 0.00** | 100 |
| Compound (14) | 50 | 0.00 ± 0.00** | 100 |
| Compound (15) | 50 | 0.00 ± 0.00** | 100 |

TABLE 9

| Test compound | Dose (mg/kg, p.o.) | Ulcer index (mm) (mean ± S.E.) | % Inhibition |
|---|---|---|---|
| Control (untreated) | — | 7.22 ± 0.36 | — |
| Compound (17) | 50 | 2.48 ± 0.68** | 65.65 |

TABLE 10

| Test compound | Dose (mg/kg, p.o.) | Ulcer index (mm) (mean ± S.E.) | % Inhibition |
|---|---|---|---|
| Control (untreated) | — | 5.98 ± 1.96 | — |

TABLE 10-continued

| Test compound | Dose (mg/kg, p.o.) | Ulcer index (mm) (mean ± S.E.) | % Inhibition |
|---|---|---|---|
| Compound (18) | 50 | 0.98 ± 0.98 | 83.16 |

TABLE 11

| Test compound | Dose (mg/kg, p.o.) | Ulcer index (mm) (mean ± S.E.) | % Inhibition |
|---|---|---|---|
| Control (untreated) | — | 6.12 ± 1.76 | — |
| Compound (31) | 50 | 0.00 ± 0.00** | 100 |

TABLE 12

| Test compound | Dose (mg/kg, p.o.) | Ulcer index (mm) (mean ± S.E.) | % Inhibition |
|---|---|---|---|
| Control (untreated) | — | 9.93 ± 0.91 | — |
| Cimetidine | 200 | 2.18 ± 1.04** | 78.0 |
| Teprenone | 100 | 0.37 ± 0.37** | 96.3 |
| " | 50 | 0.85 ± 0.61** | 91.4 |
| " | 25 | 2.15 ± 1.26** | 78.4 |
| Sofalcone | 300 | 0.00 ± 0.00** | 100 |
| " | 100 | 5.98 ± 1.04* | 39.8 |
| " | 50 | 6.13 ± 0.91* | 38.3 |
| " | 25 | 7.37 ± 0.54 | 25.8 |

Note
*Significantly different from the control group (p < 0.05, t-test)
**Significantly different from the control group (p < 0.01, t-test)

As apparent from Tables 1 to 12, all of the test compounds had inhibitory effects on peptic ulcer models, and the anti-peptic ulcer activities of the compounds according to the present invention were several times higher than the activities of control drugs cimetidine, sofalcone and teprenone.

Thus, the 3,4-dihydrobenzopyran derivative of general formula (I-1), the 3,4-dihydrobenzopyran derivative of the following general formula (I-21), which is subsumed in the 3,4-dihydrobenzopyran derivative of general formula (I-2), and their pharmacologically acceptable salts have characteristics which are of value as anti-peptic ulcer agents.

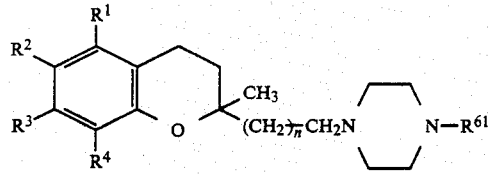

(I-21)

wherein $R^1$, $R^2$, $R^3$, $R^4$ and n have the same meanings as defined hereinbefore; $R^{61}$ means

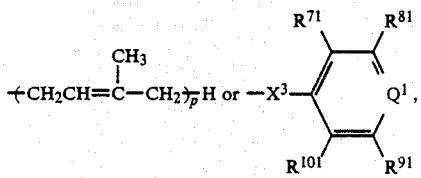

where p, $R^{71}$, $R^{81}$, $R^{91}$, $R^{101}$, $Q^1$ and $X^3$ have the same meanings as defined hereinbefore.

Of these compounds, particularly the 3,4-dihydrobenzopyran derivative of general formula (I-1), the 3,4-dihydrobenzopyran derivative of the following general formula (I-22), and their pharmacologically acceptable salts display excellent inhibitory activity against peptic ulcer.

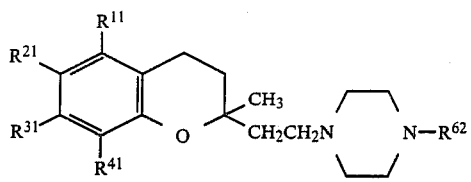

wherein $R^{11}$, $R^{31}$ and $R^{41}$ each means a lower alkyl group; $R^{21}$ means a lower alkoxyl group; $R^{62}$ means

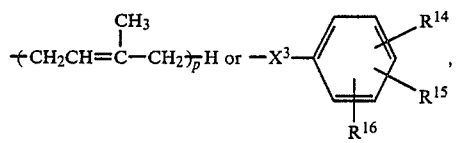

where p and $X^3$ have the same meanings as defined hereinbefore and $R^{14}$, $R^{15}$ and $R^{16}$ each means a lower alkoxyl group and are present in the 2,3,4- or 3,4,5-positions of the benzene ring.

The experimental study conducted on the relative expectorant action of the 3,4-dihydrobenzopyran compound [I] and eprazinone hydrochloride, a control drug, and the results of the study are set forth below.

Method

Male Wistar rats (body weights, 280-320 g) were used in groups of 7 animals. Each test compound was orally administered in dose of 50 mg/kg body weight to rats. Immediately after administration, 0.3 ml/100 g (body weight of rat) of a 1% aqueous solution of fluorescein sodium was injected into the caudal vein. One hour after administration of the test compound, pentobarbital sodium 100 mg/kg (body weight of rat) was injected intraperitoneally so that deep anesthesia might cause the rat to die. Then, the trachea was exposed and an incision was made in the trachea. A sonde was inserted thereinto and ligation was made. To the sonde was connected a syringe containing 10 ml of a 5% solution of sodium hydrogen carbonate kept at 37° C. and 4 ml of the solution of sodium hydrogen carbonate was injected into the lung. After 5 minutes, the fluid in the lung was removed. After this procedure of injection and removal was repeated three times, the fluid removed from the lung was filtered and the filtrate was made up with water to make 20 ml. The intensity of fluroescence was determined at the excitation wave length of 491 nm and the fluorescence wave length of 510 nm using a spectrophotometer (HITACHI model 650-10, Hitachi, Ltd.). The amount of fluorescein sodium secreted into the trachea was estimated from the intensity of fluorescence. Each test compound was administered as suspended in a gum arabic solution in concentration of 5%.

Results

The relation between each test compound and the tracheal secretion of fluorescein sodium is shown in Tables 13, 14, 15 and 16.

TABLE 13

| Test compound | Secretory amount [μg/100 g (body weight of rat)/hr] mean ± S.E. |
|---|---|
| Control (untreated) | 5.30 ± 0.40 |

TABLE 13-continued

| Test compound | Secretory amount [μg/100 g (body weight of rat)/hr] mean ± S.E. |
|---|---|
| Compound (17) | 7.90 ± 0.72** |
| Compound (19) | 8.12 ± 0.58** |
| Compound (29) | 5.57 ± 0.36 |
| Compound (30) | 5.45 ± 0.54 |
| Compound (32) | 5.43 ± 0.72 |
| Eprazinone hydrochloride | 5.26 ± 0.40 |

TABLE 14

| Test compound | Secretory amount [μg/100 g (body weight of rat)/hr] mean ± S.E. |
|---|---|
| Control (untreated) | 1.60 ± 0.18 |
| Compound (24) | 2.74 ± 0.22* |
| Compound (25) | 3.08 ± 0.19** |
| Compound (28) | 3.28 ± 0.31** |
| Eprazinone hydrochloride | 2.67 ± 0.18* |

TABLE 15

| Test compound | Secretory amount [μg/100 g (body weight of rat)/hr] mean ± S.E. |
|---|---|
| Control (untreated) | 5.20 ± 0.78 |
| Compound (17) | 9.44 ± 1.14** |
| Compound (20) | 8.72 ± 1.45* |
| Compound (21) | 5.89 ± 0.40 |
| Compound (22) | 6.26 ± 0.32 |
| Compound (23) | 8.16 ± 1.03* |
| Compound (26) | 9.61 ± 0.83** |
| Compound (27) | 6.45 ± 0.72 |

TABLE 16

| Test compound | Secretory amount [μg/100 g (body weight of rat)/hr] mean ± S.E. |
|---|---|
| Control (untreated) | 6.455 ± 0.766 |
| Compound (31) | 7.529 ± 0.751 |
| Compound (35) | 10.297 ± 1.841 |
| Eprazinone hydrochloride | 5.736 ± 0.369 |

Note
*Significantly different from the control group (p < 0.05)
**Significantly different from the control group (p < 0.01)

As apparent from Tables 13 through 16, all of the test compounds showed expectorant activity and the expectorant actions of the compounds according to the present invention were equivalent or superior to the action of the control drug eprazinone hydrochloride.

Thus, the 3,4-dihydrobenzopyran derivatives of the following general formula (I-23), which is subsumed in the 3,4-dihydrobenzopyran derivative of general formula (I-2), and pharmacologically acceptable salts thereof have characteristics which are of value as expectorants.

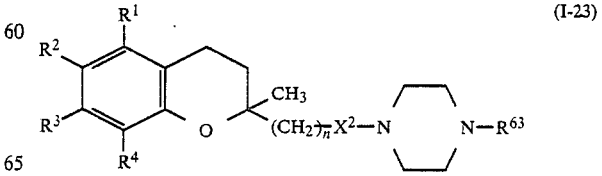

wherein $R^1$, $R^2$, $R^3$, $R^4$, $X^2$ and n have the same meanings as defined hereinbefore; $R^{63}$ when $X^2$ is a methylene group means a lower alkyl group optionally substituted by a hydroxyl group,

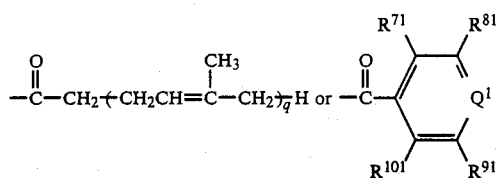

and when $X^2$ is a carbonyl group means

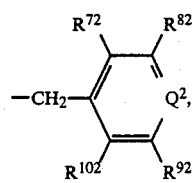

where a, $R^{71}$, $R^{81}$, $R^{91}$, $R^{101}$, $Q^1$, $R^{72}$, $R^{82}$, $R^{92}$, $R^{102}$ and $Q^2$ have the same meanings as defined hereinbefore.

Among the above compounds, particularly the 3,4-dihydrobenzopyran derivatives of the following general formula (I-24) and the 3,4-dihydrobenzopyran derivatives of the following general formula (I-25) and pharmacologically acceptable salts thereof display remarkable expectorant activity.

(I-24)

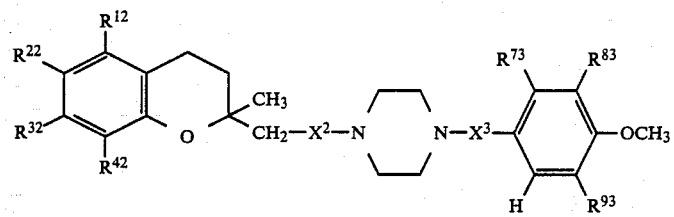

wherein $R^{73}$, $R^{83}$ and $R^{93}$ each means a hydrogen atom or a methoxy group; when all of $R^{73}$, $R^{83}$ and $R^{93}$ mean hydrogen atoms, either one of $X^2$ and $X^3$ means a methylene group with the other meaning a carbonyl group, all of $R^{12}$, $R^{32}$ and $R^{42}$ mean hydrogen atoms and $R^{22}$ means a chlorine atom, or all of $R^{12}$, $R^{32}$ and $R^{42}$ mean methyl groups and $R^{22}$ means a methoxy group; or when $R^{73}$ and $R^{83}$ each means a methoxy group, $R^{93}$ means a hydrogen atom, $X^2$ means a methylene group or a carbonyl group and $X^3$ means a methylene group, or when $R^{73}$ means a hydrogen atom, $R^{83}$ and $R^{93}$ each means a methoxy group, $X^2$ means a methylene group and $X^3$ means a carbonyl group, all of $R^{12}$, $R^{32}$ and $R^{42}$ mean methyl groups and $R^{22}$ means a methoxy group or all of $R^{12}$, $R^{22}$ and $R^{42}$ mean hydrogen atoms and $R^{32}$ means a methoxy group.

(I-25)

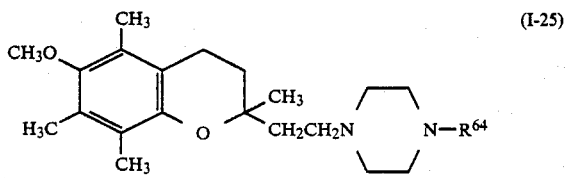

wherein $R^{64}$ means a lower alkyl group substituted by a hydroxyl group.

The experimental study conducted on the relative antitussive action of the 3,4-dihydrobenzopyran compound [I] and eprazinone hydrochloride, a control drug, and the results of the study are set forth below.

Method

Pentobarbital sodium 15 mg/kg was injected intraperitoneally to guinea pigs (body weight, 400 g or more) and under slight anesthesia, each guinea pig was immobilized in dorsal position. The skin in the anterior cervical region was incised along the midline and the trachea was exposed so as not to injure the subcutaneous tissue. A small hole was drilled in the anterior aspect of the trachea at a location 1.5 cm distant from the clavicle and through this hole a stimulating hair was inserted over a distance of 3 cm at an angle of 30° from the longitudinal axis of the trachea and, after one second, was pulled out. The stimulation was given 5 and 20 minutes after drilling of the small hole, and after occurrence of coughing was confirmed, each test compound was injected intraperitoneally. At 5 time points, i.e. 15, 30, 60, 90 and 120 minutes after injection, it was checked whether stimulation caused coughing in the same manner as described above. If coughing was not induced, even only once on the five occasions of stimulation, the test compound was regarded as effective, and if cough appeared on all the 5 occasions of stimulation, the test compound was regarded as ineffective. The $ED_{50}$ value (mg/kg) was determined by the up and down method using 10 guinea pigs [See K. A. Brownlee et al., J. Am. Stat. Assoc. 48, 262 (1953)]. As a stimulating hair, one porcine bristle, about 5 cm long, was used.

After completion of the study, the skin and wound opening of each guinea pig were fully disinfected with acrinol solution and the skin was sutured. Then, the guniea pigs were maintained as usual. The guinea pigs were not vigorous on the day following the test, with body weights decreased, but recovered after one week. After the lapse of 10 days or more, the animals were resubmitted to the test.

Results

The $ED_{50}$ values (mg/kg) of the test compounds are shown in Table 17.

TABLE 17

| Test compound | $ED_{50}$ (mg/kg) |
|---|---|
| Compound (19) | 50.14 |
| Compound (17) | 112.90 |
| Eprazinone hydrochloride | 122.47 |

It is apparent from Table 17 that the compounds according to the present invention have antitussive activity surpassing that of the control drug eprazinone hydrochloride.

Thus, the 3,4-dihydrobenzopyran derivatives of general formula (I-23), which is subsumed in the 3,4-dihydrobenzopyran derivatives of general formula (I-2), and pharmacologically acceptable salts thereof have potent antitussive activity, and particularly the 3,4-dihydrobenzopyran derivatives of general formula (I-24)

and their pharmacologically acceptable salts have very useful antitussive activity.

The 3,4-dihydrobenzopyran compound [I] has been confirmed to be low in toxicity. In regard to acute toxicity, the $LD_{50}$ value of compound (1) in mice (male mice of ddK strain, body weights 20-23 g, 10 animals per group, oral) was 3,560 mg/kg. The corresponding values of Compounds (2) to (11) were respectively more than 2,000 mg/kg, and those of compounds (12) to (36) were all more than 3,500 mg/kg.

Based on the results of the above pharmacological tests, it is clear that the 3,4-dihydrobenzopyran compounds [I] can be used as medicaments or drugs. Among these compounds, the 3,4-dihydrobenzopyran derivatives represented by general formula (I-1) and the 3,4-dihydrobenzopyran derivatives represented by general formula (I-21), as well as pharmacologically acceptable salts thereof, can be used as antiulcer agents for the prophylaxis and treatment of peptic ulcer or a prophylactic agents for gastritis caused by inflammation of the gastric mucosa. The 3,4-dihydrobenzopyran derivatives represented by general formula (I-23) and pharmacologically acceptable salts thereof can be used as antitussives and/or expectorants.

The 3,4-dihydrobenzopyran compound [I] is recommendably administered in single or divided doses in a daily dose (for human adults) of 2.5-500 mg, preferably 5-100 mg, or more preferably 5-50 mg, although the dose may vary depending on the kind of disease, the severity of condition, patient's tolerance, and other factors. Any dosage form suited for administration of said compound can be used.

The 3,4-dihydrobenzopyran compound [I] can be processed into appropriate dosage forms by the established pharmaceutical procedures. Thus, the invention includes within the scope thereof pharmaceutical compositions containing at least one of the 3,4-dihydrobenzopyran compound [I] and suitable for use as drugs for man. Such compositions can be prepared using diluents, carriers, excipients or the like, which is well known in the pharmaceutical industry, as necessary.

When the compositions are preparations for oral administration, said preparations are desirably provided in forms suitable for absorption through the gastrointestinal tract. Tablets and capsules for oral administration, which are unit dosage forms, may contain conventional auxiliaries, for example, binders, such as syrup, gum arabic, gelatin, sorbitol, gum tragacanth, polyvinylpyrrolidone, etc.; fillers, such as lactose, corn starch, calcium phosphate, sorbitol, glycine, etc.; lubricants, such as magnesium stearate, talc, polyethylene glycol, silica, etc.; disintegrators, such as potato starch; and/or acceptable wetting agents, such as sodium lauryl sulfate. The tablets may be coated by a method conventional in the art. When in liquid form, the preparations for oral administration may be as aqueous or oily suspensions, solutions, syrups, elixirs or the like or as dry preparations to be redissolved in water or some other appropriate vehicle just prior to use. Such liquid preparations may contain conventional additives, for example, suspending agents, such as sorbitol syrup, methylcellulose, glucose/sugar syrup, gelatin, hydroxyethylcellulose, carboxymethylcellulose, aluminum stearate gel, hydrogenated edible oil, etc.; emulsifiers, such as lecithin, sorbitan monooleate, gum arabic, etc.; non-aqueous vehicles, such as almond oil, fractionated coconut oil, oily esters, propylene glycol, ethyl alcohol, etc.; preservatives, such as methyl p-hydroxybenzoate, propyl p-hydroxybenzoate, sorbic acid, etc.

Injections for subcutaneous, intramuscular or intravenous administration can be prepared in the conventional manner by adding, as necessary, pH-adjusting agents, buffers, stabilizers, preservatives, solubilizing agents and so forth to the 3,4-dihydrobenzopyran compound [I].

The following examples are further illustrative of the present invention but are by no means limitative of the invention.

EXAMPLE 1

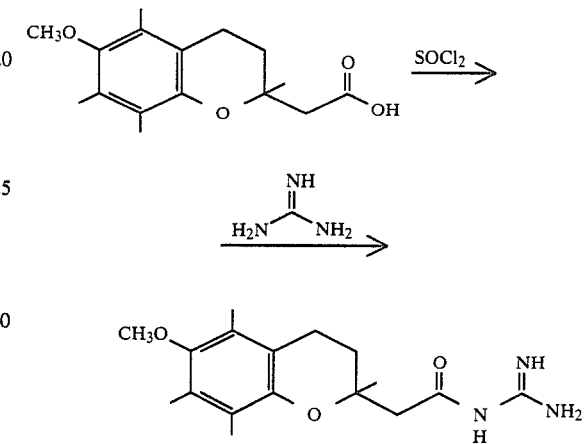

To a solution composed of 8.82 g (31.7 mmol) of (3,4-dihydro-6-methoxy-2,5,7,8-tetramethyl-2H-benzopyran-2-yl)acetic acid, 5.66 g of thionyl chloride and 20 ml of benzene was added 2 drops of N,N-dimethylformamide, and the mixture was refluxed for 2 hours. Low-boiling substances were distilled off from the reaction mixture under reduced pressure. The residue was dissolved in 20 ml of dioxane and the solution was added dropwise to a solution composed of 65 millimoles of guanidine, 7.5 ml of ethanol and 25 ml of dioxane at room temperature. Thereafter, the resultant mixture was stirred at room temperature for 1 hour and so obtained reaction mixture was poured into water and extracted with diethyl ether. The ether extract was washed with a saturated aqueous solution of sodium chloride and then dried over anhydrous sodium sulfate. Low-boiling substances were distilled off under reduced pressure. The residue was purified by silica gel column chromatography and recrystallized from methylene chloride/diethyl ether/n-hexane to give 5.1 g of N-(3,4-dihydro-6-methoxy-2,5,7,8-tetramethyl-2H-benzopyran-2-yl)-acetylguanidine [Compound (1)], which shows the following physical characteristics.

NMR spectrum (90 MHz) $\delta_{CDCl_3}^{HMS}$: 1.4 (s, 3H); 1.6-2.2 (m, 11H); 2.3-2.7 (m, 4H); 3.6 (s, 3H); 6.0 (br.s, 4H)

FD mass spectrum $[M]^+ 319$

EXAMPLES 2-8

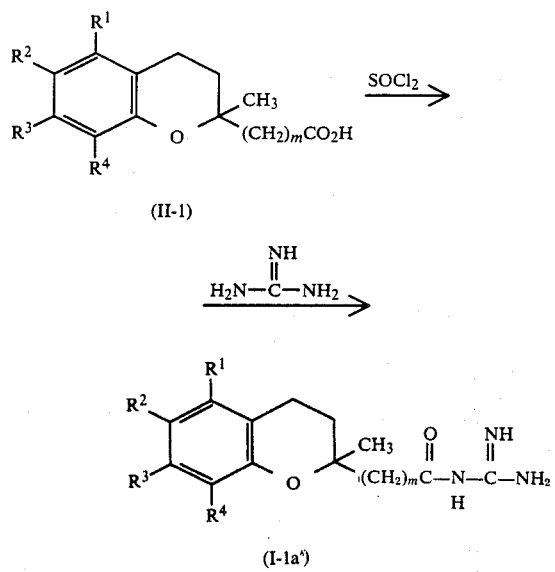

Thionyl chloride (15 mmol) was added to a solution composed of 10 millimoles of the carboxylic acid (II-1) and 10 ml of 1,2-dichloroethane and the mixture was refluxed for 3 hours. Low-boiling substances were distilled off from the reaction mixture under reduced pressure to give the corresponding carboxylic acid chloride. This carboxylic acid chloride was dissolved in 10 ml of dioxane and the solution was added dropwise to a solution composed of 60 millimoles of guanidine, 7 ml of ethanol and 20 ml of dioxane with ice cooling. The resultant mixture was stirred at room temperature overnight. The reaction mixture was poured into water and extracted with diethyl ether. The extract was dried over anhydrous sodium sulfate and low-boiling substances were distilled off under reduced pressure. The residue was purified by silica gel column chromatography to give the corresponding 3,4-dihydrobenzopyran derivative. The yield and physical characteristics of each derivative thus obtained are shown in Table 18.

TABLE 18

| Example | Compound No. | $R^1$ | $R^2$ | $R^3$ | $R^4$ | m | Yield (%) | NMR spectrum(90MHz) $\delta_{CDCl_3}^{HMS}$ | FD mass spectrum |
|---|---|---|---|---|---|---|---|---|---|
| 2 | (2) | $CH_3$ | $C_2H_5O-$ | $CH_3$ | $CH_3$ | 1 | 75.5 | 1.31(t, J=7Hz, 3H);1.40(s, 3H); 1.7~2.7(m, 15H);3.65(q, J=7Hz, 2H); 6.66(br.s, 4H) | $[M]^+333$ |
| 3 | (3) | $CH_3$ | (CH3)2C=CHCH2O— | $CH_3$ | $CH_3$ | 1 | 22.6 | 1.42(s, 3H);1.69(s, 3H);1.80(s, 3H); 1.85~2.75(m, 15H);4.15(d, J=8Hz, 2H); 5.6(t, J=8Hz, 1H);6.06(br.s, 4H) | $[M]^+373$ |
| 4 | (6) | H | $CH_3O-$ | H | H | 1 | 50.5 | 1.39(s, 3H);1.60~2.80(m, 6H); 3.66(s, 3H);6.60(s, 3H);6.5(br.s, 4H) | $[M]^+277$ |
| 5 | (7) | H | H | $CH_3O-$ | H | 1 | 46.3 | 1.35(s, 3H);1.5~2.9(m, 6H); 3.64(s, 3H);6.2~7.0(m, 3H); 7.15(br.s, 4H) | $[M]^+277$ |
| 6 | (8) | H | Cl | H | H | 1 | 59.2 | 1.39(s, 3H);1.6~2.25(m, 2H); 2.5(s, 2H);2.7(t, J=8Hz, 2H); 5.95(br.s, 4H);6.6~7.3(m, 3H) | $[M]^+281$ |
| 7 | (4) | $CH_3$ | $CH_3O-$ | $CH_3$ | $CH_3$ | 0 | 60.7 | 1.5(s, 3H);2.0~2.63(m, 13H); 3.57(s, 3H);5.73(br.s, 4H) | $[M]^+305$ |
| 8 | (5) | $CH_3$ | $CH_3O-$ | $CH_3$ | $CH_3$ | 2 | 68.7 | 1.30(s, 3H);1.55~2.2(m, 15H); 2.57(t, J=8Hz, 2H);3.63(s, 3H); 5.91(br.s, 4H) | $[M]^+333$ |

EXAMPLE 9

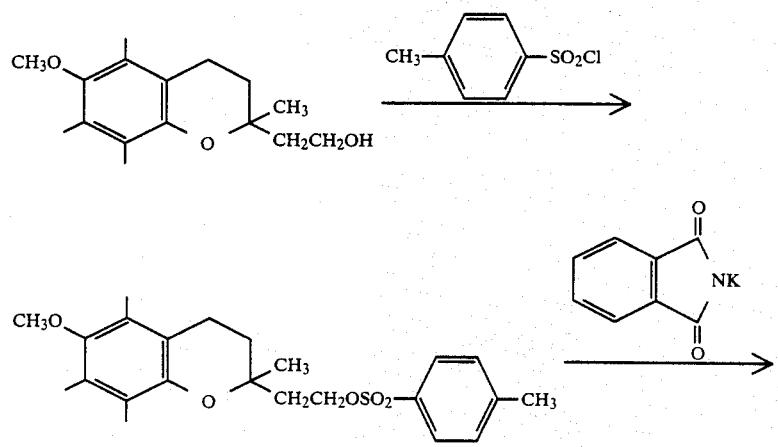

-continued

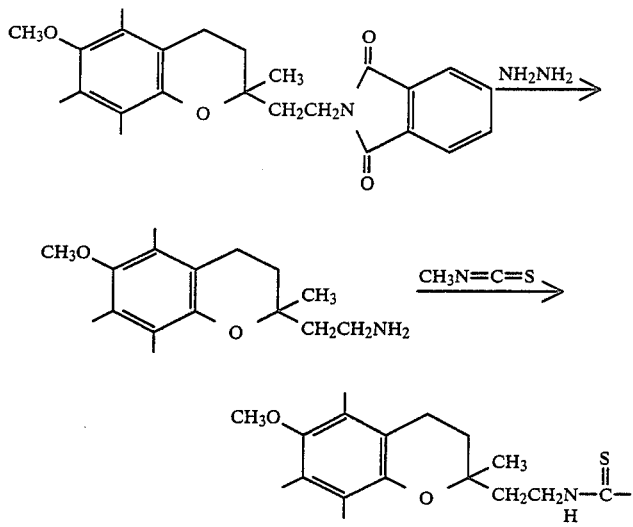

(a) Pyridine (150 ml) was added to 40 g (160 mmol) of 3,4-dihydro-2-(2-hydroxyethyl)-6-methoxy-2,5,7,8-tetramethyl-2H-benzopyran for dissolution of the latter. Then the solution was cooled to 0° C. and thereto was added with vigorous stirring 34.5 g of p-toluenesulfonyl chloride gradually. After stirring at 0° C. for 1 hour, the reaction mixture was poured into 1 liter of dilute hydrochloric acid and extracted with diethyl ether. The ether layer was washed with water, dried over anhydrous magnesium sulfate and filtered. After removal of low-boiling substances from the filtrate by distillation, the residue was purified by silica gel column chromatography to give 49.8 g (78.6% yield) of 3,4-dihydro-6-methoxy-2-[2-(p-toluenesulfonyloxy)ethyl]-2,5,7,8-tetramethyl-2H-benzopyran, which has the following FD mass spectrum.

FD mass spectrum [M]+418

(b) A 12-g portion of the 3,4-dihydro-6-methoxy-2-[2-(p-toluenesulfonyloxy)ethyl]-2,5,7,8-tetramethyl-2H-benzopyran obtained in the above manner and 6.59 g of potassium phthalimido were suspended in 50 ml of N,N-dimethylformamide. After a small amount of sodium iodide was added to the suspension, the mixture was heated at 90° C. for 40 minutes. The reaction mixture was cooled, and then water was added thereto, and the mixture was extracted with methylene chloride. The extract was washed with a dilute aqueous solution of sodium hydroxide and then with water, and dried over anhydrous sodium sulfate. Low-boiling substances were distilled off and the residue was purified by silica gel column chromatography to give 10.6 g (90.8% yield) of N-[2-(3,4-dihydro-6-methoxy-2,5,7,8-tetramethyl-2H-benzopyran-2-yl)ethyl]-phthalimide.

(c) The N-[2-(3,4-dihydro-6-methoxy-2,5,7,8-tetramethyl-2H-benzopyran-2-yl)ethyl]phthalimide (10.6 g) obtained in the above manner, 80 ml of methanol and 1.35 g of hydrazine hydrate were mixed and refluxed for 1 hour. The reaction mixture was cooled, 60 ml of water was added thereto, and the methanol was distilled off under reduced pressure. To the residue was added 60 ml of concentrated hydrochloric acid, and the mixture was refluxed for 1 hour. The reaction mixture was cooled to 0° C. and filtered. To the crystals thus obtained was added 120 ml of 1N aqueous solution of sodium hydroxide. The mixture was refluxed for 15 minutes, and the reaction mixture was cooled and extracted with diethyl ether. The extract was dried over anhydrous sodium sulfate, and low-boiling substances were distilled off under reduced pressure to give 6.1 g of 2-(3,4-dihydro-6-methoxy-2,5,7,8-tetramethyl-2H-benzopyran-2-yl)ethylamine.

(d) A 2-g portion of the 2-(3,4-dihydro-6-methoxy-2,5,7,8-tetramethyl-2H-benzopyran-2-yl)ethylamine obtained in the above manner was dissolved in 50 ml of methanol. To the solution was added dropwise 0.55 g of methyl isothiocyanate. After the addition, the resulting mixture was refluxed for 4 hours and then the methanol was distilled off under reduced pressure. Water was added to the residue, and the mixture was extracted with diethyl ether. The extract was dried over anhydrous sodium sulfate, and low-boiling substances were distilled off under reduced pressure. The residue was purified by silica gel column chromatography to give 2.3 g (90.1% yield) of N-[2-(3,4-dihydro-6-methoxy-2,5,7,8-tetramethyl-2H-benzopyran-2-yl)ethyl]-N'-methylthiourea [Compound (9)], which has the physical characteristics given below.

NMR spectrum (90 MHz) $\delta_{CDCl_3}^{HMS}$: 1.20 (s, 3H); 1.65–2.18 (m, 15H); 2.56 (t, J=8 Hz, 2H); 3.56 (s, 3H); 3.60 (br.s, 1H); 5.90 (br.s, 1H); 6.20 (br.s, 1H)

FD mass spectrum: [M+]336

EXAMPLE 10

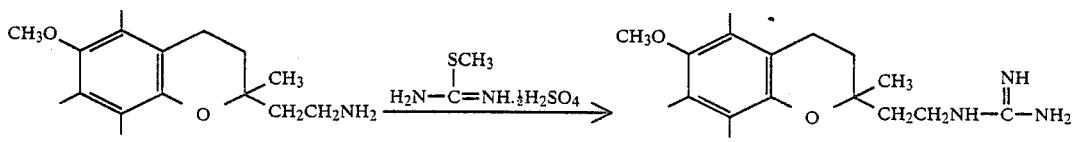

A suspension composed of 1.0 g of the 2-(3,4-dihydro-6-methoxy-2,5,7,8-tetramethyl-2H-benzopyran-2-yl)ethylamine obtained by the process of Example 9-(c), 0.52 g of methylisothiourea sulfate and 20 ml of ethanol was refluxed for 6 hours, followed by removal of low-boiling substances by distillation under reduced pressure. A dilute aqueous solution of sodium hydroxide to the residue and the resultant mixture was extracted with diethyl ether. The extract was dried over anhydrous sodium sulfate and then low-boiling substances were distilled off under reduced pressure. The residue was purified by silica gel column chromatography to give 0.5 g of N-[2-(3,4-dihydro-6-methoxy-2,5,7,8-tetramethyl-2H-benzopyran-2-yl)ethyl]guanidine [Compound (10)] having the following physical characteristics.

NMR spectrum (90 MHz) $\delta_{DMSO, TFA, CDCl_3}^{HMS}$: 1.20 (s, 3H); 1.63-2.15 (m, 15H); 2.60 (m, 2H); 2.95 (br.s, 2H); 3.52 (s, 3H); 7.67 (br.s, 2H)

FD mass spectrum: [M+1]+306

EXAMPLE 11

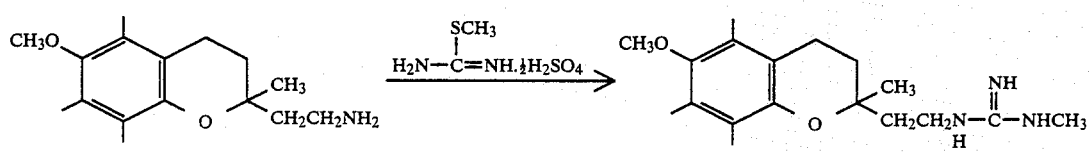

A suspension composed of 2.0 g of the 2-(3,4-dihydro-6-methoxy-2,5,7,8-tetramethyl-2H-benzopyran-2-yl)ethylamine obtained by the process of Example 9-(c), 4.2 g of methylisothiourea sulfate and 20 ml of methanol was refluxed for 20 hours, followed by removal of low-boiling substances by distillation under reduced pressure. A dilute aqueous solution of sodium hydroxide was added to the residue and the resultant mixture was extracted with diethyl ether. The extract was dried over anhydrous sodium sulfate and then low-boiling substances were distilled off under reduced pressure. The residue was purified by silica gel column chromatography to give 1.27 g (52.3% yield) of N-[2-(3,4-dihydro-6-methoxy-2,5,7,8-tetramethyl-2H-benzopyran-2-yl)ethyl]-N'-methylguanidine [Compound (11)] having the following physical characteristics.

NMR spectrum (90 MHz) $\delta_{CDCl_3}^{HMS}$: 1.20 (s, 3H); 1.5-2.2 (m, 13H); 2.52 (t, J=7 Hz, 2H); 3.16 (t, J=8 Hz, 2H); 3.57 (s, 3H); 3.63 (s, 3H); 4.66 (br.s, 3H)

FD mass spectrum: [M+1]+320

EXAMPLE 12

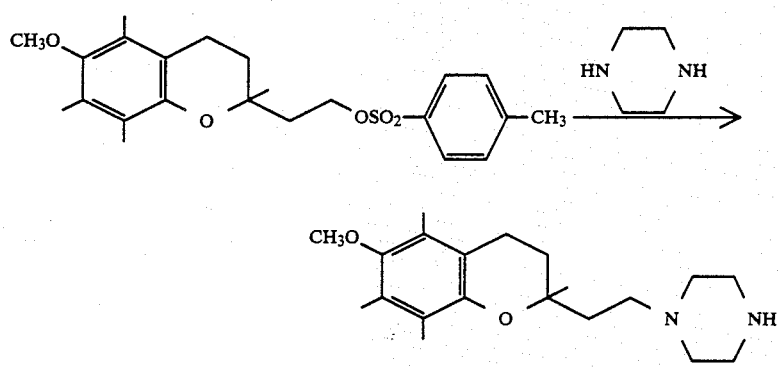

Piperazine (61.7 g, 0.718 mole) was dissolved in 300 ml of toluene, and 30 g (0.0718 mole) of the 3,4-dihydro-6-methoxy-2-[2-(p-toluenesulfonyloxy)ethyl]2,5,7,8-tetramethyl-2H-benzopyran obtained by the process of Example 9-(a) was added to the solution with refluxing. Thereafter, the mixture was refluxed for 3 hours. After cooling, the reaction mixture was poured into water and extracted with diethyl ether. The ether layer was dried over anhydrous sodium sulfate. Low-boiling substances were distilled off under reduced pressure and then the excess piperazine was removed by sublimation under reduced pressure. The residue thus obtained was purified by silica gel column chromatography to give 14.1 g of 3,4-dihydro-6-methoxy-2-[2-(piperazin-1-yl)ethyl]-2,5,7,8-tetramethyl-2H-benzopyran [Compound (12)] having the following physical characteristics.

NMR spectrum (90 MHz) $\delta_{CDCl_3}^{HMS}$: 1.22 (s, 3H); 1.55-1.90 (m, 4H); 2.02 (s, 3H); 2.08 (s, 3H); 2.14 (s, 3H); 2.18 (s, 1H); 2.26-2.68 (m, 8H); 2.70-2.96 (m, 4H); 3.57 (s, 3H)

FD mass spectrum: [M]+332

EXAMPLES 13-16

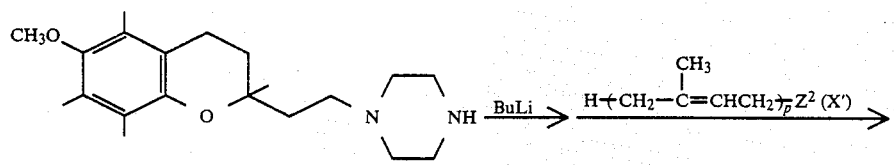

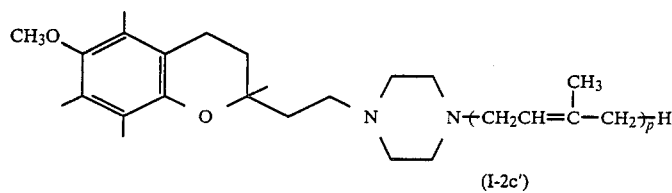

(I-2c')

A solution composed of 2 g (6.02 mmol) of the 3,4-dihydro-6-methoxy-2-[2-(piperazin-1-yl)ethyl]-2,5,7,8-tetramethyl-2H-benzopyran obtained by the process of Example 12 and 50 ml of tetrahydrofuran was cooled to cal characteristics for each derivative thus obtained are shown in Table 19.

TABLE 19

| Example | Halogenated terpene compound (X') P | Halogenated terpene compound (X') $Z^2$ | 3,4 Dihydrobenzopyran derivative (I-2c') Product | 3,4 Dihydrobenzopyran derivative (I-2c') Yield (%) | 3,4 Dihydrobenzopyran derivative (I-2c') NMR spectrum (90 MHz) $\delta^{HMS}_{CDCl_3}$ | FD mass spectrum |
|---|---|---|---|---|---|---|
| 13 | 1 | Cl | Compound (13) | 78.9 | 1.20(s, 3H); 1.53~1.83(m, 10H); 2.00(s, 3H); 2.05(s, 3H); 2.10(s, 3H); 2.26~2.67(m, 12H); 2.87(d, J = 7Hz, 2H); 3.54(s, 3H); 5.19(t, J = 7Hz, 1H) | [M]+ 400 |
| 14 | 2 | Br | compound (14) | 80.5 | 1.20(s, 3H); 1.5~2.20(m, 26H); 2.3~2.67(m, 12H); 2.9(d, J = 7Hz, 2H); 3.54(s, 3H); 4.9~5.35(m, 2H) | [M]+ 468 |
| 15 | 3 | Br | compound (15) | 75.6 | 1.17(s, 3H); 1.47~2.20(m, 33H); 2.33~2.67(m, 12H); 2.94(d, J = 7Hz, 2H); 3.55(s, 3H); 4.90~5.35(m, 3H) | [M]+ 536 |
| 16 | 4 | Br | compound (16) | 82.5 | 1.20(s, 3H); 1.45~1.84(m, 18H); 1.85~2.19(m, 18H); 2.30~2.67(m, 12H); 2.90(d, J = 7Hz, 2H); 3.53(s, 3H); 4.90~5.33(m, 4H) | [M]+ 604 |

−40° C. in a nitrogen atmosphere and, to this solution, 4.7 ml of a 15% solution of n-butyllithium in hexane was added gradually. The resultant mixture was stirred at −40° C. for 30 minutes. Then, 6.65 millimoles of the halogenated terpene compound (X') was added gradually thereto, and the resultant mixture was stirred at −40° C. for 30 minutes. After raising the temperature gradually to room temperature, the reaction mixture was poured into water and extracted with diethyl ether. The ether layer was dried over anhydrous sodium sulfate, and low-boiling substances were distilled off under reduced pressure. The residue was purified by silica gel column chromatography to give the corresponding 3,4-dihydrobenzopyran derivative. The yield and physi-

EXAMPLE 17

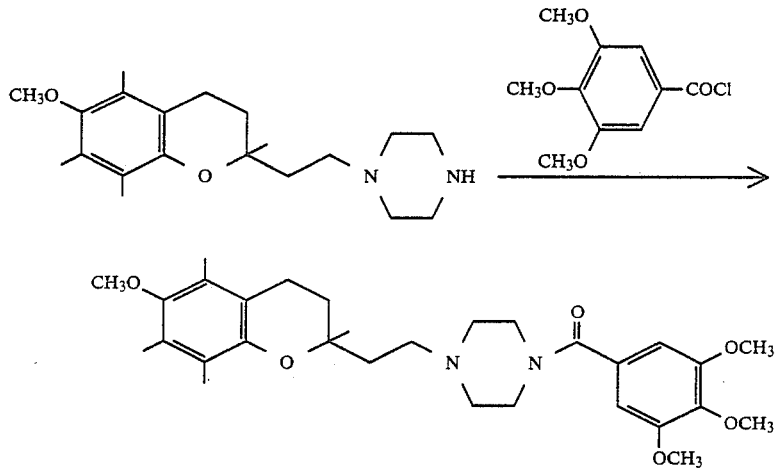

A solution composed of 2.0 g (6.02 mmol) of the 3,4-dihydro-6-methoxy-2-[2-(piperazin-1-yl)ethyl]-2,5,7,8-tetramethyl-2H-benzopyran obtained by the process of Example 12, 50 ml of 1,2-dichloroethane and 0.57 g of pyridine was ice-cooled in a nitrogen atmosphere and, to this solution, 1.67 g of 3,4,5-trimethoxybenzoyl chloride was added dropwise. The resultant mixture was stirred at room temperature overnight. The reaction mixture was then poured into water and extracted with diethyl ether. The ether layer was dried over anhydrous sodium sulfate. Low-boiling substances were distilled off under reduced pressure and the residue was purified by silica gel column chromatography to give 1.99 g of 3,4-dihydro-6-methoxy-2-[2-[4-(3,4,5-trimethoxybenzoyl)piperazin-1-yl]ethyl]-2,5,7,8-tetramethyl-2H-benzopyran [Compound (17)] having the following physical characteristics.

(m, 12H); 3.37 (s, 2H); 3.55 (s, 3H); 3.80 (s, 9H); 6.50 (s, 2H)

FD mass spectrum: [M]+ 512

EXAMPLE 19

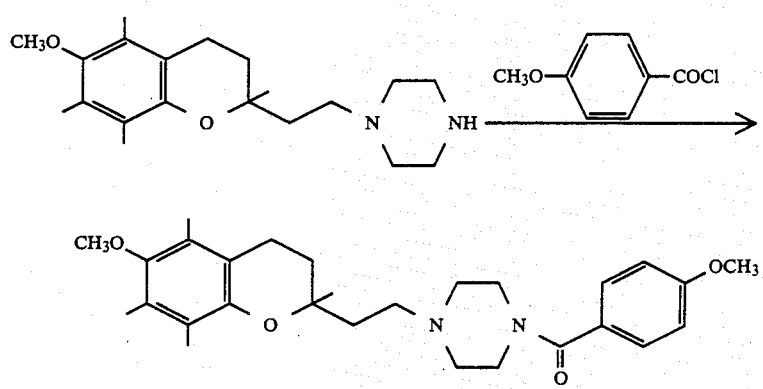

NMR spectrum (90 MHz) $\delta_{CDCl_3}{}^{HMS}$: 1.18 (s, 3H); 1.57-1.90 (m, 4H); 2.00 (s, 3H); 2.05 (s, 3H); 2.10 (s, 3H); 2.25-2.65 (m, 8H); 3.35-3.92 (m, 16H); 6.57 (s, 2H)

FD mass spectrum: [M]+ 526

EXAMPLE 18

To a solution composed of 2.5 g (7.53 mmol) of the 3,4-dihydro-6-methoxy-2-[2-(piperazin-1-yl)ethyl]-2,5,7,8-tetramethyl-2H-benzopyran, 0.72 g of pyridine and 7.5 ml of 1,2-dichloroethane, there was added dropwise 1.54 g (9.01 mmol) of 4-methoxybenzoyl chloride. The resultant mixture was stirred overnight at room

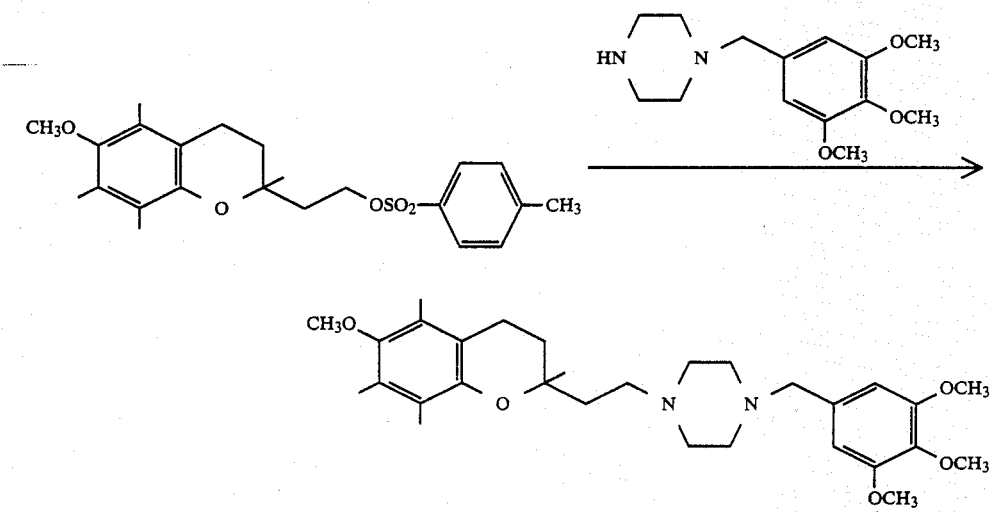

A solution composed of 10.8 g (25.8 mmol) of the 3,4-dihydro-6-methoxy-2-[2-(p-toluenesulfonyloxy)ethyl]-2,5,7,8-tetramethyl-2H-benzopyran obtained in the same manner as in Example 9-(a), 12.4 g (46.1 mmol) of N-(3,4,5-trimethoxybenzyl)piperazine and 215 ml of toluene was refluxed for 5 hours. The reaction mixture was poured into water and extracted with two portions of diethyl ether. The ether layers were combined and dried over anhydrous sodium sulfate. Low-boiling substances were distilled off under reduced pressure and the residue was purified by silica gel column chromatography to give 7.12 g of 3,4-dihydro-6-methoxy-2-[2-[4-(3,4,5-trimethoxybenzyl)piperazin-1-yl]ethyl]-2,5,7,8-tetramethyl-2H-benzopyran [Compound (18)] having the following physical characteristics.

NMR spectrum (90 MHz) $\delta_{CDCl_3}{}^{HMS}$: 1.18 (s, 3H); 1.51-1.87 (m, 4H); 2.04 (s, 6H); 2.07 (s, 3H); 2.30-2.70 temperature. The reaction mixture was poured into water and extracted with diethyl ether. The extract was washed with a saturated aqueous solution of sodium chloride and dried over anhydrous sodium sulfate. Low-boiling substances were distilled off under reduced pressure and the residue obtained was purified by silica gel column chromatography to give 1.4 g (39.9% yield) of 1-[2-(3,4-dihydro-6-methoxy-2,5,7,8-tetramethyl-2H-benzopyran-2-yl)ethyl]-4-(4-methoxybenzoyl)-piperazine [Compound (19)] having the following physical characteristics.

NMR spectrum (90 MHz) $\delta_{CDCl_3}{}^{HMS}$: 1.18 (s, 3H); 1.60-1.86 (m, 4H); 2.01 (s, 3H); 2.06 (s, 3H); 2.11 (s, 3H); 2.26-2.65 (m, 8H); 3.38-3.67 (m, 7H); 3.77 (s, 3H); 6.83 (d, J=9 Hz, 2H); 7.32 (d, J=9 Hz, 2H)

FD mass spectrum: [M]+ 466

EXAMPLES 20-24

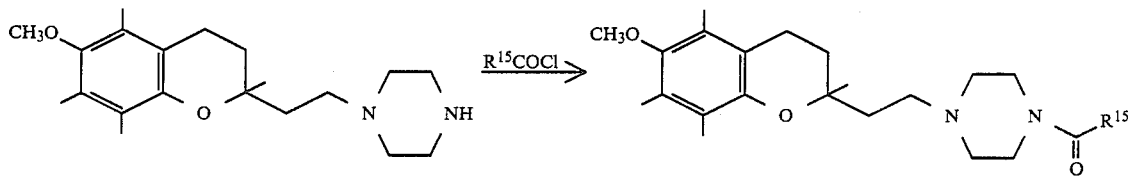

The reaction and separation-purification procedures of Example 19 were followed using 9.01 millimoles of 4-dimethylaminobenzoyl chloride, 4-nitrobenzoyl chloride, 4-bromobenzoyl chloride, 4-pyridylcarbonyl chloride or 5,9,13-trimethyl-4,8,12-tetradecatrienoyl chloride in lieu of 1.54 g (9.01 mmol) of 4-methoxybenzoyl chloride to give the corresponding 1-[2-(3,4-dihydro-6-methoxy-2,5,7,8-tetramethyl-2H-benzopyran-2-yl)ethyl]-4-(4-dimethylaminobenzoyl)piperazine [Compound (20)], 1-[2-(3,4-dihydro-6-methoxy-2,5,7,8-tetramethyl-2H-benzopyran-2-yl)ethyl]-4-(4-nitrobenzoyl)piperazine [Compound (21)], 1-[2-(3,4-dihydro-6-methoxy-2,5,7,8-tetramethyl-2H-benzopyran-2-yl)ethyl]-4-(4-bromobenzoyl)piperazine [Compound (22)], 1-[2-(3,4-dihydro-6-methoxy-2,5,7,8-tetramethyl-2H-benzopyran-2-yl)ethyl]-4-(4-pyridylcarbonyl)piperazine [Compound (23)] and 1-[2-(3,4-dihydro-6-methoxy-2,5,7,8-tetramethyl-2H-benzopyran-2-yl)ethyl]-4-(5,9,13-trimethyl-4,8,12-tetradecatrienoyl)piperazine [Compound (24)], respectively. The yield and physical characteristics for each product are shown in Table 20.

TABLE 20

| Example | Product | Yield (%) | NMR spectrum (90 MHz) $\delta^{HMS}_{CDCl_3}$ | FD mass spectrum |
|---|---|---|---|---|
| 20 | Compound (20) | 33.2 | 1.20 (s, 3H); 1.56–1.87 (m, 4H); 2.02 (s, 3H); 2.07 (s, 3H); 2.14 (s, 3H); 2.29–2.67 (m, 8H); 2.93 (s, 6H); 3.47–3.65 (m, 7H); 6.61 (d, J = 9Hz, 2H); 7.30 (d, J = 9Hz, 2H) | [M]$^+$ 479 |
| 21 | Compound (21) | 65.6 | 1.21 (s, 3H); 1.56–1.86 (m, 4H); 2.01 (s, 3H); 2.07 (s, 3H); 2.11 (s, 3H); 2.20–2.67 (m, 8H); 3.17–3.83 (m, 7H); 7.50 (d, J = 9Hz, 2H); 8.24 (d, J = 9Hz, 2H) | [M]$^+$ 481 |
| 22 | Compound (22) | 61.2 | 1.21 (s, 3H); 1.60–1.95 (m, 4H); 2.02 (s, 3H); 2.08 (s, 3H); 2.12 (s, 3H); 2.23–2.68 (m, 8H); 3.20–3.79 (m, 7H); 7.17–7.57 (m, 4H) | [M]$^+$ 514 |
| 23 | Compound (23) | 30.4 | 1.21 (s, 3H); 1.60–1.85 (m, 4H); 2.01 (s, 3H); 2.07 (s, 3H); 2.12 (s, 3H); 2.22–2.70 (m, 8H); 3.17–3.74 (m, 7H); 7.27 (d, J = 8Hz, 2H); 8.67 (d, J = 8Hz, 2H) | [M]$^+$ 437 |
| 24 | Compound (24) | 60.6 | 1.21 (s, 3H); 1.50–2.70 (m, 45H); 3.33–3.73 (m, 4H); 3.56 (s, 3H); 4.95–5.29 (br.s, 3H) | [M]$^+$ 578 |

EXAMPLE 25

(a)

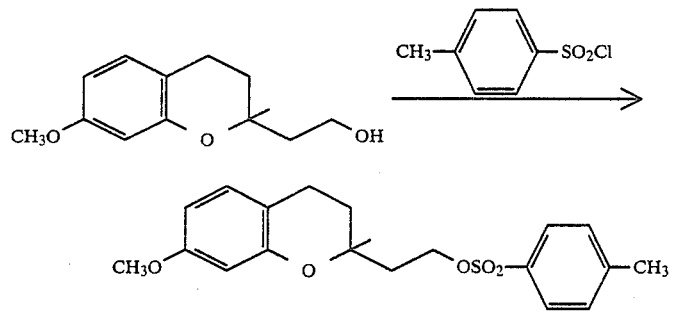

The reaction and separation-purification procedures of Example 9-(a) were followed using 35.5 g (160 mmol) of 3,4-dihydro-2-(2-hydroxyethyl)-7-methoxy-2-methyl-2H-benzopyran in lieu of 40 g (160 mmol) of 3,4-dihydro-2-(2-hydroxyethyl)-6-methoxy-2,5,7,8-tetramethyl-2H-benzopyran to give 43.2 g (71.8% yield) of 3,4-dihydro-7-methoxy-2-methyl-2-[2-(p-toluenesulfonyloxy)ethyl]-2H-benzopyran.

(b)

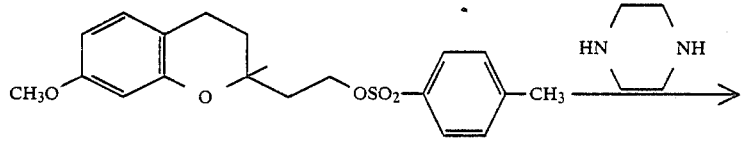

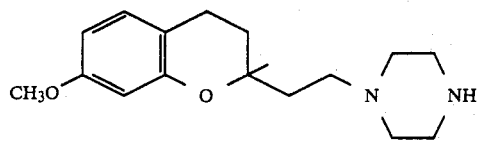

The reaction and separation-purification procedures of Example 12 were followed using 27 g (0.0718 mol) of the 3,4-dihydro-7-methoxy-2-methyl-2-[2-(p-toluenesulfonyloxy)ethyl]-2H-benzopyran obtained in the above manner in lieu of 30 g (0.0718 mol) of 3,4-dihydro-6-methoxy-2-[2-(p-toluenesulfonyloxy)ethyl]-2,5,7,8-tetramethyl-2H-benzopyran to give 18.8 g (90.3% yield) of 3,4-dihydro-7-methoxy-2-methyl-2-[2-(piperazin-1-yl)ethyl]-2H-benzopyran.

(c)

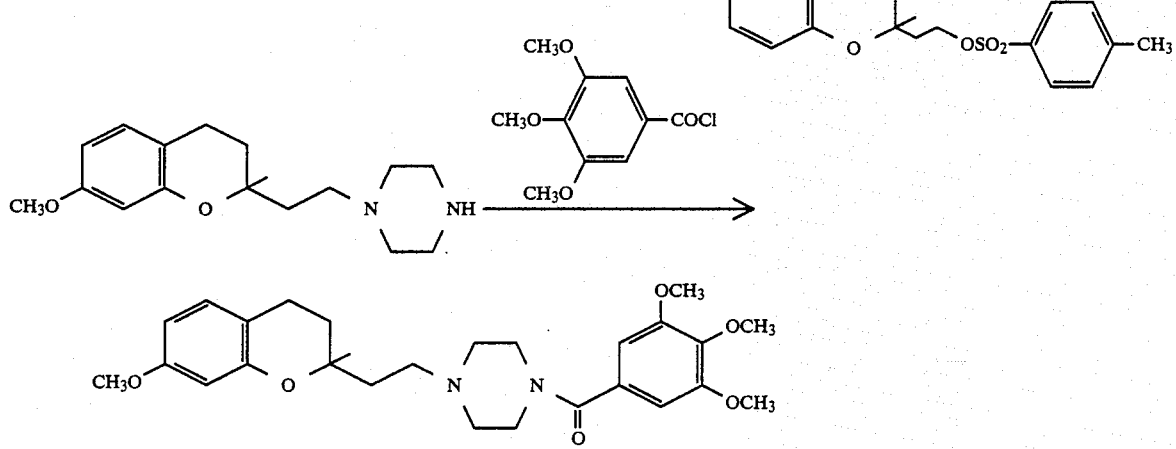

3,4,5-Trimethoxybenzoyl chloride (6.7 g, 0.029 mol) was added dropwise to a solution composed of 7.0 g (0.0241 mol) of 3,4-dihydro-7-methoxy-2-methyl-2-[2-(piperazin-1-yl)ethyl]-2H-benzopyran, 2.28 g of pyridine and 100 ml of 1,2-dichloroethane. The resultant mixture was stirred at room temperature for 2 hours. The reaction mixture obtained was poured into water and extracted with diethyl ether, the extract was dried over anhydrous sodium sulfate, and low-boiling substances were distilled off under reduced pressure. The residue was purified by silica gel column chromatography to give 5.0 g of 1-[2-(3,4-dihydro-7-methoxy-2-methyl-2H-benzopyran-2-yl)ethyl]-4-(3,4,5-trimethoxybenzoyl)piperazine [Compound (25)] having the following physical characteristics.

NMR spectrum (90 MHz) $\delta_{CDCl_3}^{HMS}$: 1.24 (s, 3H); 1.60–1.90 (m, 4H); 2.27–2.75 (m, 8H); 3.40–3.73 (m, 7H); 3.83 (s, 9H); 6.23–7.00 (m, 5H)

FD mass spectrum: [M]+ 484

EXAMPLE 26

(a)

In a nitrogen atmosphere, 11.0 g (0.0495 mol) of 6-chloro-3,4-dihydro-2-(2-hydroxyethyl)-2-methyl-2H-benzopyran was dissolved in 50 ml of pyridine, the solution was cooled to 0° C. and, with vigorous stirring, 11.3 g of p-toluenesulfonyl chloride was added gradually thereto. After stirring at 0° C. for 1 hour, the reaction mixture was poured into 300 ml of dilute hydrochloric acid and extracted with diethyl ether. The ether layer was washed with water, dried over anhydrous magnesium sulfate and filtered. Low-boiling substances were distilled off from the filtrate under reduced pressure, and the residue was purified by silica gel column chromatography to give 15.3 g of 6-chloro-3,4-dihydro-2-methyl-2-[2-(p-toluenesulfonyloxy)ethyl]-2H-benzopyran.

(b)

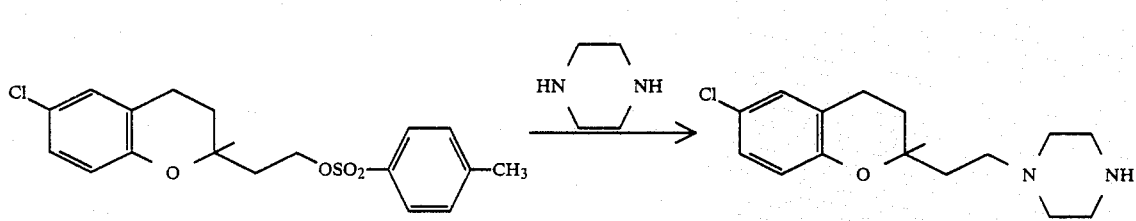

Piperazine (35 g, 0.40 mol) was dissolved in 200 ml of toluene. To the solution was added, with refluxing, 15.3 g (0.04 mol) of the 6-chloro-3,4-dihydro-2-methyl-2-[2-(p-toluenesulfonyloxy)ethyl]-2H-benzopyran obtained in the above manner. After refluxing the mixture for 5 hours, the reaction mixture was cooled and poured into water, followed by extraction with diethyl ether. The ether layer was dried over anhydrous sodium sulfate. Low-boiling substances were distilled off under reduced pressure and the excess piperazine was then removed by sublimation under reduced pressure. The residue obtained was purified by silica gel column chromatography to give 9.4 g of 6-chloro-3,4-dihydro-2-methyl-2-[2-(piperazin-1-yl)ethyl]-2H-benzopyran having the following physical characteristics.

NMR spectrum (90 MHz) $\delta_{CDCl_3}^{HMS}$: 1.23 (s, 3H); 1.60–1.97 (m, 4H); 2.23–2.96 (m, 13H); 6.55–7.28 (m, 4H)

(c)

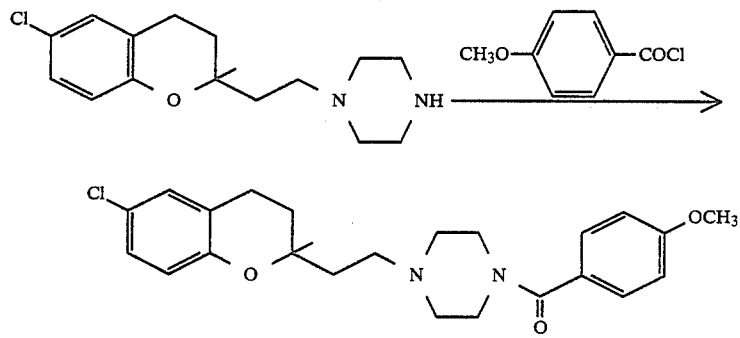

To a solution composed of 2.3 g (7.81 mmol) of the 6-chloro-3,4-dihydro-2-methyl-2-[2-(piperazin-1-yl)ethyl]-2H-benzopyran obtained in the above manner, 0.74 g of pyridine and 50 ml of 1,2-dichloroethane, there was added dropwise 1.60 g (9.37 mmol) of 4-methoxybenzoyl chloride. After overnight stirring at room temperature, the reaction mixture was poured into water and extracted with diethyl ether. The extract was washed with a saturated aqueous solution of sodium chloride and dried over anhydrous sodium sulfate. Low-boiling substances were distilled off under reduced pressure and the residue was purified by silica gel column chromatography to give 1.6 g (47.8% yield) of 1-[2-(6-chloro-3,4-dihydro-2-methyl-2H-benzopyran-2-yl)ethyl]-4-(4-methoxybenzoyl)piperazine [Compound (26)] having the following physical characteristics.

NMR spectrum (90 MHz) $\delta_{CDCl_3}^{HMS}$: 1.23 (s, 3H); 1.63–1.90 (m, 4H); 2.20–2.81 (m, 8H); 3.46–3.70 (m, 4H); 3.79 (s, 3H); 6.58–7.46 (m, 7H)

FD mass spectrum: [M]+ 428

EXAMPLE 27

(a)

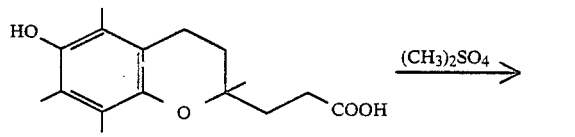

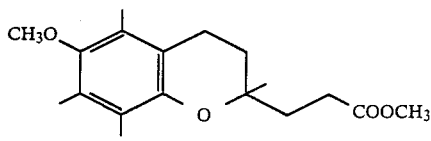

An aqueous solution of potassium hydroxide (7.1 g in 10 ml of water) was added dropwise to a solution composed of 10 g (0.036 mol) of 3-(3,4-dihydro-6-hydroxy-2,5,7,8-tetramethyl-2H-benzopyran-2-yl)propionic acid and 200 ml of ethanol in a nitrogen atmosphere and the mixture was stirred at room temperature for 30 minutes. The ethanol was distilled off from the reaction mixture under reduced pressure, toluene was added to the residue, and dehydration was effected azeotropically under reduced pressure. To the residue thus obtained, 200 ml of N,N-dimethylformamide was added for dissolution of the residue. To the solution was added dropwise, with vigorous stirring, 4.53 g (3.4 ml) of dimethyl sulfate while maintaining the solution at a temperature of room temperature to 50° C. After the addition, the reaction was conducted at 50° C. for 5 hours. After cooling to room temperature, the reaction mixture was poured into dilute hydrochloric acid and extracted with diethyl ether. The extract was washed with water and then with a saturated aqueous solution of sodium chloride, dried over anhydrous magnesium sulfate and then filtered. Low-boiling substances were distilled off from the filtrate under reduced pressure and the residue was purified by silica gel column chromatography to give 5.9 g (53.6% yield) of methyl 3-(3,4-dihydro-6-methoxy-2,5,7,8-tetramethyl-2H-benzopyran-2-yl)propionate.

(b)

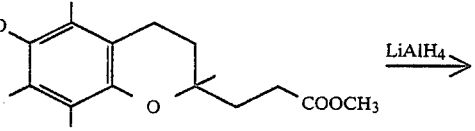

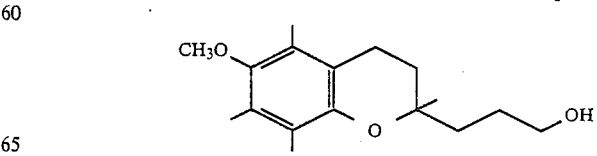

In a nitrogen atmosphere, 0.73 g of lithium aluminum hydride was added to 20 ml of dried tetrahydrofuran and, while refluxing the mixture, a solution of 5.9 g (0.0193 mol) of methyl 3-(3,4-dihydro-6-methoxy-2,5,7,8-tetramethyl-2H-benzopyran-2-yl)propionate in 10 ml of tetrahydrofuran was added dropwise slowly thereto, followed by refluxing for 1 hour. After cooling, the reaction mixture was poured into dilute hydrochloric acid and extracted with two portions of diethyl ether. The combined extracts were washed with a saturated aqueous solution of sodium chloride, dried over anhydrous magnesium sulfate and filtered. Low-boiling substances were distilled off from the filtrate under reduced pressure. The residue was purified by silica gel column chromatography to give 3.8 g of 3,4-dihydro-6-methoxy-2-[3-(p-toluenesulfonyloxy)-propyl]-2,5,7,8-tetramethyl-2H-benzopyran.

(d)

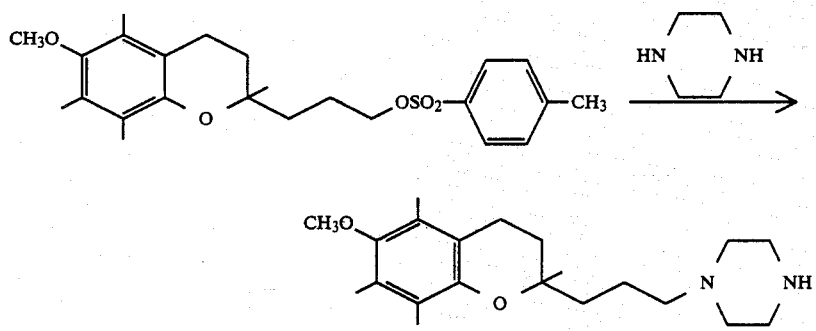

rated aqueous solution of sodium chloride, dried over anhydrous magnesium sulfate and filtered. Low-boiling substances were distilled off from the filtrate under reduced pressure, whereupon 5.0 g of crude 3,4-dihydro-2-(3-hydroxypropyl)-6-methoxy-2,5,7,8-tetramethyl-2H-benzopyran was obtained.

(c)

To a refluxing solution of 7.2 g (0.085 mol) of piperazine in 50 ml of toluene was added 3.8 g (8.5 mmol) of the 3,4-dihydro-6-methoxy-2-[3-(p-toluenesulfonyloxy)-propyl]-2,5,7,8-tetramethyl-2H-benzopyran obtained in the above manner, followed by refluxing for 6 hours. After cooling, the reaction mixture was poured into water and extracted with diethyl ether. The ether layer

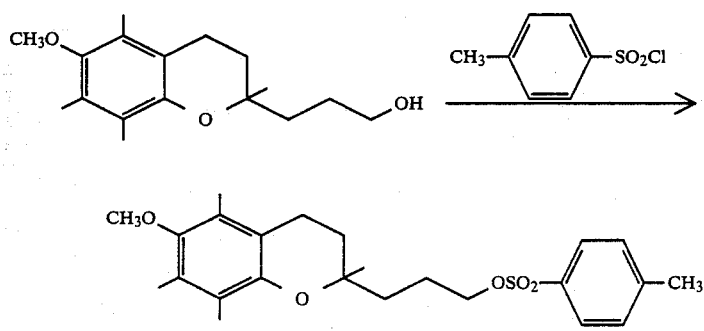

The crude 3,4-dihydro-2-(3-hydroxypropyl)-6-methoxy-2,5,7,8-tetramethyl-2H-benzopyran (5.0 g) obtained in the above manner was dissolved in 50 ml of pyridine and the solution was cooled to 0° C. To the solution was added slowly 3.9 g of p-toluenesulfonyl chloride with vigorous stirring. After stirring at 0° C. for 1 hour, the reaction mixture was poured into 100 ml of dilute hydrochloric acid and extracted with diethyl ether. The ether layer was washed with water and then was dried over anhydrous sodium sulfate and low-boiling substances were distilled off therefrom under reduced pressure and the excess piperazine was then removed by sublimation under reduced pressure. The thus-obtained residue was purified by silica gel column chromatography to give 2.7 g (91.8% yield) of 3,4-dihydro-6-methoxy-2-[3-(piperazin-1-yl)propyl]-2,5,7,8-tetramethyl-2H-benzopyran.

(e)

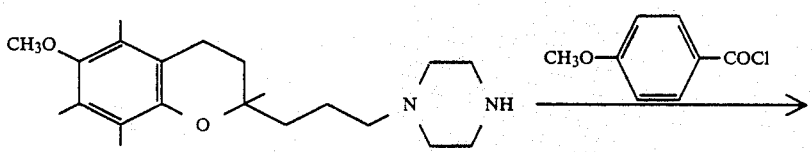

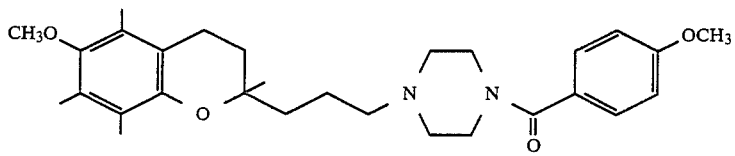

4-Methoxybenzoyl chloride (1.59 g, 9.36 mmol) was added dropwise to a solution composed of 2.7 g (7.8 mmol) of the 3,4-dihydro-6-methoxy-2-[3-(piperazin-1-yl)propyl]-2,5,7,8-tetramethyl-2H-benzopyran obtained in the above manner, 0.74 g of pyridine and 10 ml of 1,2-dichloroethane. After overnight stirring at room temperature, the reaction mixture was poured into water and extracted with diethyl ether. The extract was washed with a saturated aqueous solution of sodium chloride and dried over anhydrous sodium sulfate. Low-boiling substances were distilled off under reduced pressure and the residue was purified by silica gel column chromatography to give 0.8 g (21.4% yield) of 1-[3-(3,4-dihydro-6-methoxy-2,5,7,8-tetramethyl-2H-benzopyran-2-yl)propyl]-4-(4-methoxybenzoyl)piperazine [Compound (27)] having the following physical characteristics.

NMR spectrum (90 MHz) $\delta_{CDCl_3}^{HMS}$: 1.19 (s, 3H); 1.45–1.85 (m, 6H); 2.01 (s, 3H); 2.09 (s, 3H); 2.13 (s, 3H); 2.25–2.66 (m, 8H); 3.46–3.66 (m, 7H); 3.77 (s, 3H); 6.85 (d, J=9 Hz, 2H); 7.33 (d, J=9 Hz, 2H)

FD mass spectrum: [M]+ 480

EXAMPLE 28

(a)

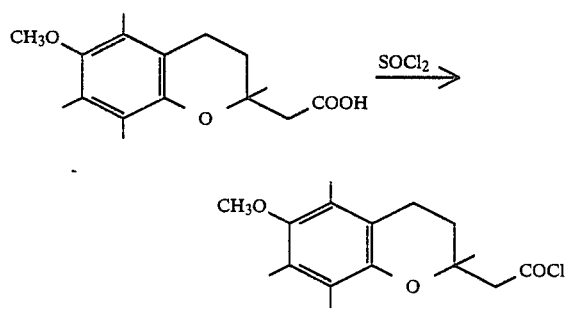

To a solution composed of 3.34 g of (3,4-dihydro-6-methoxy-2,5,7,8-tetramethyl-2H-benzopyran-2-yl)acetic acid, 2 drops of N,N-dimethylformamide and 50 ml of benzene was added 0.87 ml of thionyl chloride, and the mixture was refluxed for 2 hours. After cooling, the reaction mixture was evaporated under reduced pressure to remove the low-boiling substances. The above procedure gave (3,4-dihydro-6-methoxy-2,5,7,8-tetramethyl-2H-benzopyran-2-yl)acetyl chloride in a quantitative yield of 3.56 g.

(b)

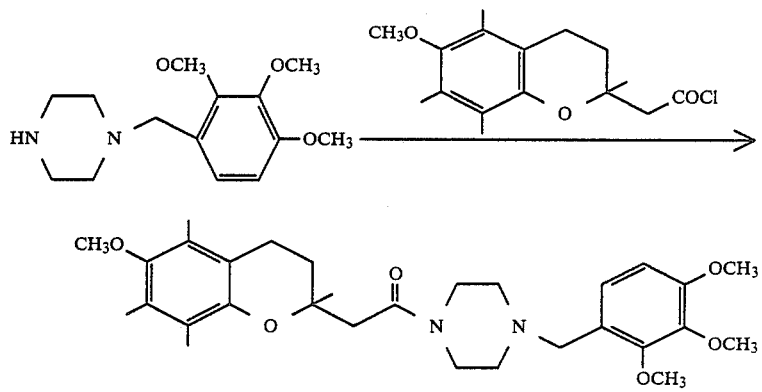

To a solution composed of 2.54 g (0.01 mol) of 1-(2,3,4-trimethoxyphenyl)methylpiperazine, 0.95 g of pyridine and 50 ml of 1,2-dichloroethane was added 3.56 g (0.012 mol) of the (3,4-dihydro-6-methoxy-2,5,7,8-tetramethyl-2H-benzopyran-2-yl)acetyl chloride prepared above and the mixture was stirred at room temperature overnight. The reaction mixture was poured into water and extracted with diethyl ether. The extract was washed with water and then with a saturated aqueous solution of sodium chloride, dried over anhydrous sodium sulfate and filtered. Low-boiling substances were distilled off from the filtrate under reduced pressure and the residue was purified by silica gel column chromatography. The eluate was further purified by recrystallization from a 95:5 (v/v) mixture of hexane and ethyl acetate to give 1.4 g of 1-[(3,4-dihydro-6-methoxy-2,5,7,8-tetramethyl-2H-benzopyran-2-yl)acetyl]-4-(2,3,4-trimethoxybenzyl)piperazine [Compound (28)] having the following physical characteristics.

NMR spectrum (90 MHz) $\delta_{CDCl_3}^{HMS}$: 1.33 (s, 3H); 1.80–2.20 (m, 11H); 2.26–2.73 (m, 8H); 3.35–3.70 (m, 9H); 3.83 (s, 9H); 6.57 (d, J=9 Hz, 1H); 6.92 (d, J=9 Hz, 1H)

FD mass spectrum: [M]+526

EXAMPLE 29

(a)

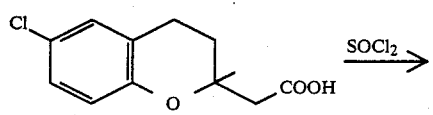

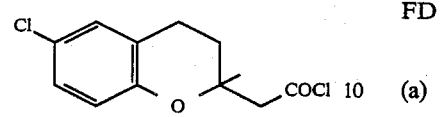

To a solution composed of 2.89 g of (6-chloro-3,4-dihydro-2-methyl-2H-benzopyran-2-yl)acetic acid, 2 drops of N,N-dimethylformamide and 50 ml of benzene was added 0.9 ml of thionyl chloride and the mixture was refluxed for 2 hours. After cooling, the reaction mixture was evaporated under reduced pressure to remove the low-boiling substances. The above procedure gave (6-chloro-3,4-dihydro-2-methyl-2H-benzopyran-2-yl)acetyl chloride in a quantitative yield of 3.1 g.

(b)

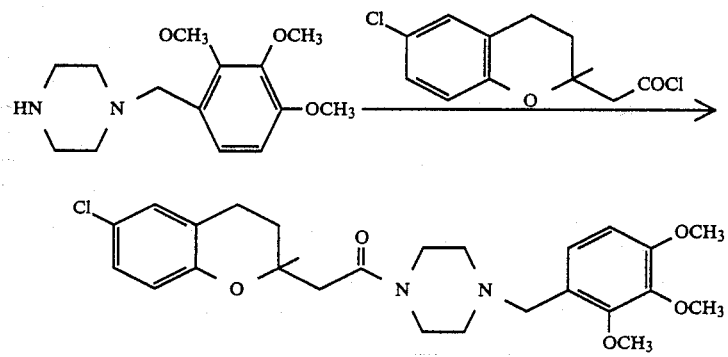

To a solution composed of 2.54 g (0.01 mol) of 1-(2,3,4-trimethoxyphenyl)methylpiperazine, 0.95 g of pyridine and 50 ml of 1,2-dichloroethane was added 3.1 g (0.012 mol) of the (6-chloro-3,4-dihydro-2-methyl-2H-benzopyran-2-yl)acetyl chloride prepared above and the mixture was stirred at room temperature overnight. The reaction mixture was poured into water and extracted with diethyl ether. The extract was washed with water and then with a saturated aqueous solution of sodium chloride, dried over anhydrous sodium sulfate and filtered. The filtrate was evaporated under reduced pressure to remove the low-boiling substances and the residue was purified by silica gel column chromatography. The above procedure gave 3.4 g (69.6% yield) of 1-[(6-chloro-3,4-dihydro-2-methyl-2H-benzopyran-2-yl)acetyl]-4-(2,3,4-trimethoxybenzyl)piperazine [Compound (29)] having the following physical characteristics.

NMR spectrum (90 MHz) $\delta_{CDCl_3}^{HMS}$: 1.34 (s, 3H); 1.80–2.06 (m, 2H); 2.28–2.53 (m, 4H); 2.57–2.82 (m, 4H); 3.35–3.70 (m, 6H); 3.80 (s, 9H); 6.50–7.07 (m, 5H)

FD mass spectrum: [M]+ 488

EXAMPLE 30

(a)

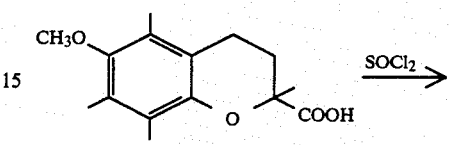

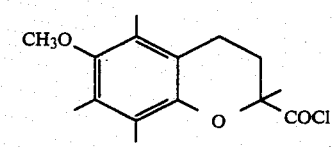

To a solution composed of 3.0 g of (3,4-dihydro-6-methoxy-2,5,7,8-tetramethyl-2H-benzopyran-2-yl)carboxylic acid, 2 drops of N,N-dimethylformamide and 50 ml of 1,2-dichloroethane was added 1.1 ml of thionyl chloride and the mixture was refluxed for 2 hours. After cooling, the reaction mixture was evaporated under reduced pressure to remove the low-boiling substances. This procedure gave (3,4-dihydro-6-methoxy-2,5,7,8-tetramethyl-2H-benzopyran-2-yl)carbonyl chloride in a quantitative yield of 3.39 g.

(b)

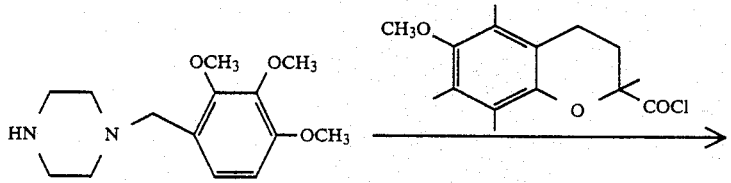

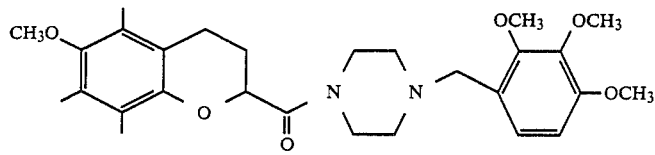

To a solution composed of 2.54 g (0.01 mol) of 1-(2,3,4-trimethoxyphenyl)methylpiperazine, 0.95 g of pyridine and 50 ml of 1,2-dichloroethane was added 3.39 g of the (3,4-dihydro-6-methoxy-2,5,7,8-tetramethyl-2H-benzopyran-2-yl)carbonyl chloride prepared above and the mixture was stirred at room temperature for 1 hour. The reaction mixture was poured into water and extracted with diethyl ether. The extract was washed with water and then with a saturated aqueous solution of sodium chloride, dried over anhydrous sodium sulfate and filtered. The filtrate was evaporated under reduced pressure to remove the low-boiling substances and the residue was purified by silica gel column chromatography. The eluate was further purified by recrystallization from a 95:5 (v/v) mixture of hexane and diethyl ether to give 3.4 g (66% yield) of 1-[(3,4-dihydro-6-methoxy-2,5,7,8-tetramethyl-2H-benzopyran-2-yl)carbonyl]-4-(2,3,4-trimethoxybenzyl)piperazine [Compound (30)] having the following physical characteristics.

NMR spectrum (90 MHz) $\delta_{CDCl_3}^{HMS}$: 1.53 (s, 3H); 1.64–2.67 (m, 21H); 3.36 (s, 2H); 3.59 (s, 3H); 3.81 (s, 9H); 6.58 (d, J=9 Hz, 1H); 6.91 (d, J=9 Hz, 1H)

FD mass spectrum: [M]+ 512

EXAMPLE 31

To a solution composed of 2.5 g (7.53 mmol) of the 3,4-dihydro-6-methoxy-2-[2-(piperazin-1-yl)ethyl]-2,5,7,8-tetramethyl-2H-benzopyran obtained by the process of Example 12, 0.72 g of pyridine and 50 ml of 1,2-dichloroethane was added dropwise 1.27 g (9.04 mmol) of benzoyl chloride and the mixture was stirred at room temperature overnight. The reaction mixture was poured into 100 ml of a 2% (wt) aqueous solution of sodium hydroxide and extracted with ethyl acetate. The extract was washed with a saturated aqueous solution of sodium chloride and dried over anhydrous sodium sulfate. Low-boiling substances were distilled under reduced pressure, and the residue was purified by silica gel column chromatography to give 2.4 g (73% yield) of 1-benzoyl-4-[2-(3,4-dihydro-6-methoxy-2,5,7,8-tetramethyl-2H-benzopyran-2-yl)ethyl]piperazine [Compound (32)] having the following physical characteristics.

NMR spectrum (90 MHz) $\delta_{CDCl_3}^{HMS}$: 1.22 (s, 3H); 1.45–1.91 (m, 4H); 2.05 (s, 3H); 2.09 (s, 3H); 2.14 (s, 3H); 2.26–2.71 (m, 8H); 3.40–3.76 (m, 7H); 7.39 (s, 5H)

FD mass spectrum: [M]+ 436

EXAMPLE 32

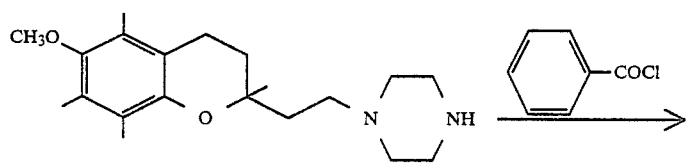

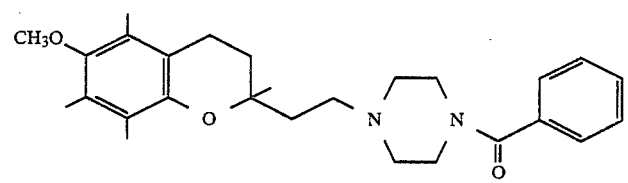

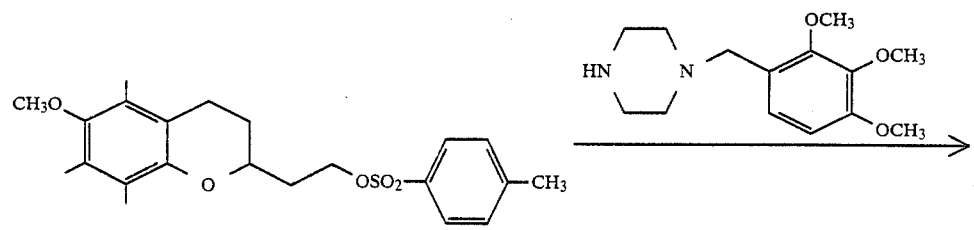

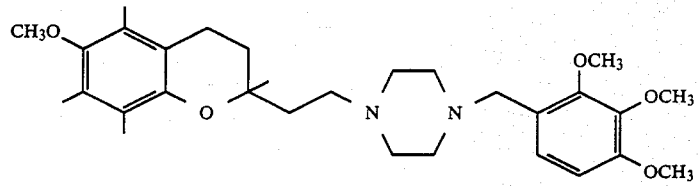

A solution composed of 10.8 g of 3,4-dihydro-6-methoxy-2-[2-(p-toluenesulfonyloxy)ethyl]-2,5,7,8-tetramethyl-2H-benzopyran, 12.4 g of N-(2,3,4-trimethoxybenzyl)piperazine and 215 ml of toluene was refluxed for 5 hours in a nitrogen atmosphere. After cooling to room temperature, the reaction mixture was poured into water and extracted with diethyl ether. The extract was washed with two portions of water and dried over anhydrous sodium sulfate. Low-boiling substances were distilled off under reduced pressure and the residue was purified by silica gel column chromatography. The eluate was further purified by recrystallization from hexane to give 7.12 g (53.8% yield) of 1-[2-(3,4-dihydro-6-methoxy-2,5,7,8-tetramethyl-2H-benzopyran-2-yl)ethyl]-4-(2,3,4-trimethoxybenzyl)piperazine [Compound (31)] having the following physical characteristics.

NMR spectrum (90 MHz) $\delta_{CDCl_3}^{HMS}$: 1.17 (s, 3H); 1.55–1.93 (m, 4H); 2.00 (s, 3H); 2.06 (s, 3H); 2.11 (s, 3H); 2.26–2.69 (m, 12H); 3.40 (s, 2H); 3.56 (s, 3H); 3.80 (s, 9H); 6.56 (d, J=8 Hz, 1H); 6.93 (d, J=8 Hz, 1H)

FD mass spectrum: [M]+ 512

EXAMPLE 33

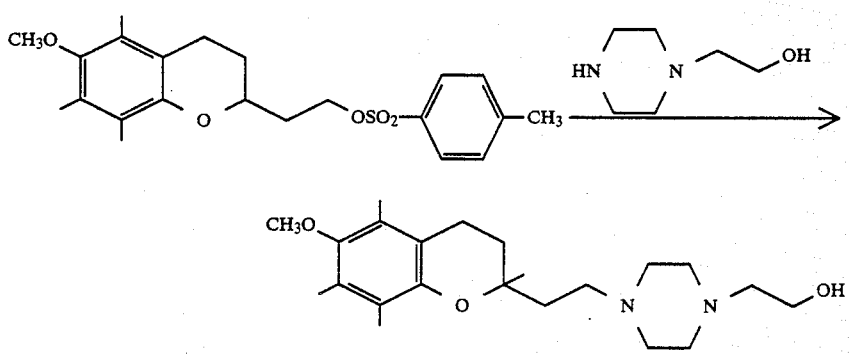

A solution composed of 20 g of N-(2-hydroxyethyl)piperazine, 5 g of 3,4-dihydro-6-methoxy-2-[2-(p-toluenesulfonyloxy)ethyl]-2,5,7,8-tetramethyl-2H-benzopyran and 100 ml of toluene was refluxed for 8 hours in a nitrogen atmosphere. After cooling to room temperature, the reaction mixture was poured into water and extracted with diethyl ether. The extract was washed with water and dried over anhydrous sodium sulfate. Low-boiling substances were distilled off under reduced pressure and the residue was purified by silica gel column chromatography to give 3.66 g of 1-[2-(3,4-dihydro-6-methoxy-2,5,7,8-tetramethyl-2H-benzopyran-2-yl)ethyl]-4-(2-hydroxyethyl)piperazine [Compound (35)] having the following physical characteristics.

NMR spectrum (90 MHz) $\delta_{CDCl_3}^{HMS}$: 1.23 (s, 3H); 1.60–1.96 (m, 4H); 2.05 (s, 3H); 2.10 (s, 3H); 2.16 (s, 3H); 2.36–2.74 (m, 14H); 3.46–3.73 (m, 5H); 4.05–4.44 (br.s, 1H)

FD mass spectrum: [M]+ 376

EXAMPLES 34 AND 35

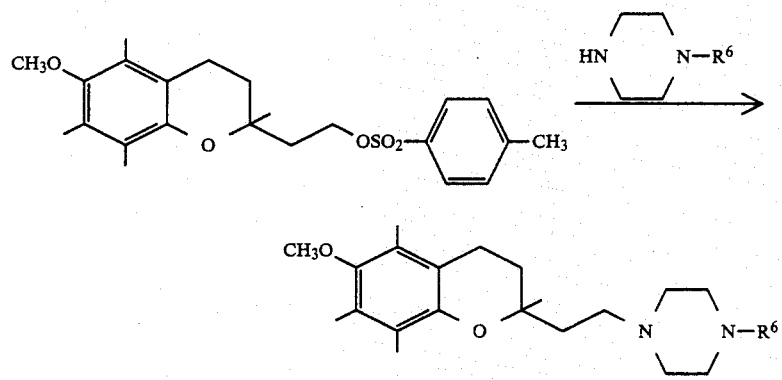

The reaction and separation-purification procedures of Example 33 were followed using 20 g of N-methylpiperazine or 20 g of N-(3-hydroxypropyl)piperazine in lieu of 20 g of N-(2-hydroxyethyl)piperazine to give the corresponding 1-[2-(3,4-dihydro-6-methoxy-2,5,7,8-tetramethyl-2H-benzopyran-2-yl)ethyl]-4-methylpiperazine [Compound (33)] and 1-[2-(3,4-dihydro-6-methoxy-2,5,7,8-tetramethyl-2H-benzopyran-2-yl)ethyl]-4-(3-hydroxypropyl)piperazine [Compound (36)], respectively. The yield and physical characteristics for each product are shown in Table 21.

TABLE 21

| Example | Product | Yield (g) | NMR spectrum (90 MHz) $\delta_{CDCl_3}^{HMS}$ | FD mass spectrum |
|---|---|---|---|---|
| 34 | Compound (33) | 3.78 | 1.19 (s, 3H); 2.53–2.93 (m, 4H); 2.01 (s, 3H); 2.05 (s, 3H); 2.10 (s, 3H); 2.25–2.73 (m, 15H); 3.60 (s, 3H) | [M]+ 346 |
| 35 | Compound (36) | 3.51 | 1.22 (s, 3H); 1.56–1.95 (m, 6H); 2.01 (s, 3H); 2.06 (s, 3H); 2.11 (s, 3H); 2.21–2.82 (m, 14H); 3.40–3.77 (m, 5H); 3.90–4.59 (br.s, 1H) | [M]+ 390 |

EXAMPLE 36

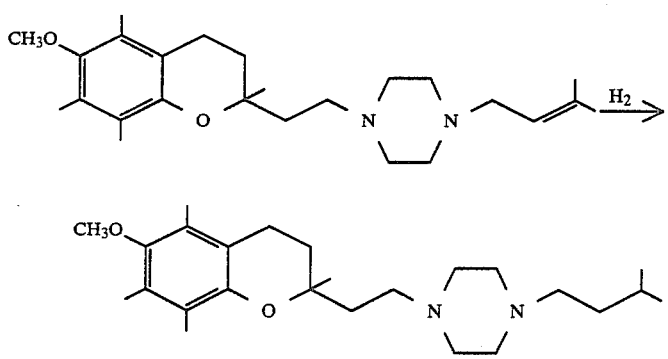

A solution composed of 2.0 g of the 3,4-dihydro-6-methoxy-2-[2-[4-(3-methyl-2-butenyl)piperazin-1-yl]ethyl]-2,5,7,8-tetramethyl-2H-benzopyran obtained by the process of Example 13, 0.1 g of 5% palladium on carbon and 50 ml of ethanol was stirred at room temperature for 48 hours. The reaction mixture was filtered to remove the palladium on carbon and low-boiling substances were distilled off under reduced pressure. The residue was purified by silica gel column chromatography to give 1.24 g of 1-[2-(3,4-dihydro-6-methoxy-2,5,7,8-tetramethyl-2H-benzopyran-2-yl)ethyl]-4-isopentylpiperazine [Compound (34)] having the following physical characteristics.

NMR spectrum (90 MHz) $\delta_{CDCl_3}^{HMS}$: 1.20 (s, 3H); 1.47–1.87 (m, 13H); 1.99 (s, 3H); 2.04 (s, 3H); 2.10 (s, 3H); 2.26–3.01 (m, 14H); 3.53 (s, 3H)

FD mass spectrum: [M]+ 402

Examples of manufacture of pharmaceutical products containing the following compounds of the present invention, for instance, are described below.

N-(3,4-Dihydro-6-methoxy-2,5,7,8-tetramethyl-2H-benzopyran-2-yl)acetylguanidine [Compound (1)]

3,4-Dihydro-6-methoxy-2-[2-(piperazin-1-yl)ethyl]-2,5,7,8-tetramethyl-2H-benzopyran [Compound (12)]

3,4-Dihydro-6-methoxy-2-[2-[4-(3,4,5-trimethoxybenzoyl)piperazin-1-yl]ethyl]-2,5,7,8-tetramethyl-2H-benzopyran [Compound (17)]

1-[2-(3,4-Dihydro-6-methoxy-2,5,7,8-tetramethyl-2H-benzopyran-2-yl)ethyl]-4-(4-methoxybenzoyl)piperazine [Compound (19)]

EXAMPLE 37

Tablets

| Compound (1) | 25 g |
|---|---|
| Corn starch | 55 g |
| Carboxycellulose | 15 g |
| Polyvinylpyrrolidone | 3 g |
| Calcium stearate | 2 g |
| Total | 100 g |
| Compound (12) | 25 g |
| Corn starch | 55 g |
| Carboxycellulose | 15 g |
| Polyvinylpyrrolidone | 3 g |
| Calcium stearate | 2 g |
| Total | 100 g |
| Compound (17) | 25 g |
| Corn starch | 55 g |
| Carboxycellulose | 15 g |
| Polyvinylpyrrolidone | 3 g |
| Calcium stearate | 2 g |
| Total | 100 g |
| Compound (19) | 25 g |
| Corn starch | 55 g |
| Carboxycellulose | 15 g |
| Polyvinylpyrrolidone | 3 g |
| Calcium stearate | 2 g |
| Total | 100 g |

Tablets, 100 mg per tablet, were manufactured in accordance with the established pharmaceutical procedure. Each tablet contained 25 mg of Compound (1), Compound (12), Compound (17) or Compound (19).

EXAMPLE 38

Powders and Capsules

| Compound (1) | 25 g |
|---|---|
| Crystalline cellulose | 75 g |
| Total | 100 g |
| Compound (12) | 25 g |
| Crystalline cellulose | 75 g |
| Total | 100 g |

| | | |
|---|---|---|
| Compound (19) | 25 g | |
| Crystalline cellulose | 75 g | |
| Total | 100 g | |

Powders of the two components were admixed to provide powders. Further, 100 mg portions of each product powder were filled into No. 5 hard capsules to provide capsules.

What is claimed is:

1. A 3,4-dihydrobenzopyran derivative of the formula

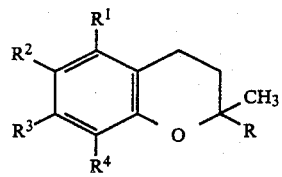
(I)

wherein $R^1$ and $R^4$ each represent a hydrogen atom or a lower alkyl group; $R^2$ represents a hydrogen atom, a halogen atom, a lower alkoxyl group or a lower alkenyloxy group; $R^3$ represents a hydrogen atom, a lower alkyl group or a lower alkoxyl group; R represents a group of the following formula (2)

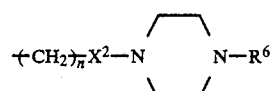
(2)

wherein n represents an integer of 0, 1 or 2; $X^2$ represents a methylene group or a carbonyl group; when $X^2$ represents a naphthylene group, $R^6$ represents a lower alkyl group or a lower alkyl group substituted by a hydroxyl group,

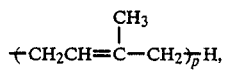

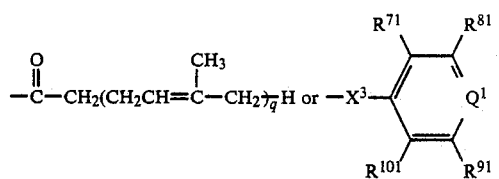

and when $X^2$ represents a carbonyl group, $R^6$ represents

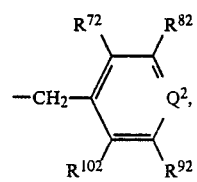

where p and q each represent an integer of 0 to 4; $X^3$ represents a methylene group or a carbonyl group; $Q^1$ represents a nitrogen atom (=N—) a carbon atom

where $R^{111}$ represents a hydrogen atom, a lower alkoxyl group, a halogen atom, a di-lower alkylamino group or a nitro group; $R^{71}$, $R^{81}$, $R^{91}$ and $R^{101}$ each represent a hydrogen atom or a lower alkoxyl group; $Q^2$ represents a nitrogen atom (=N—), a carbon atom

where $R^{112}$ represents a hydrogen atom, a lower alkoxyl group, a halogen atom, a di-lower alkylamino group or a nitro group; and $R^{72}$, $R^{82}$, $R^{92}$ and $R^{102}$ each represent a hydrogen atom or a lower alkoxyl group; or a pharmacologically acceptable salt thereof.

2. The compound of claim 1, which is a 3,4-dihydrobenzopyran derivative of the formula

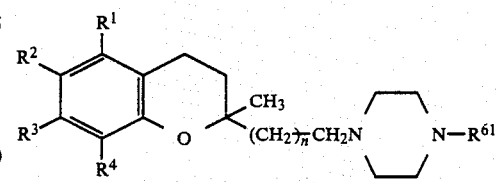
(I-21)

wherein $R^1$, $R^2$, $R^3$, $R^4$ and n have the same meanings as defined hereinbefore; $R^{61}$ represents

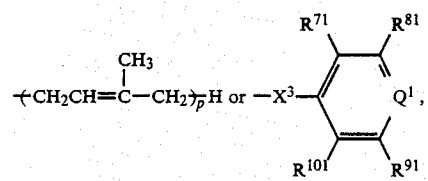

where p, $R^{71}$, $R^{81}$, $R^{91}$, $R^{101}$, $Q^1$ and $X^3$ have the same meanings as defined hereinbefore or a pharmacologically acceptable salt thereof.

3. The compound of claim 2, which is a 3,4-dihydrobenzopyran derivative of the formula

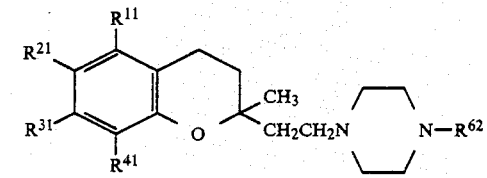
(I-22)

wherein $R^{11}$, $R^{31}$ and $R^{41}$ each represent a lower alkyl group; $R^{21}$ represents a lower alkoxyl group; $R^{62}$ represents

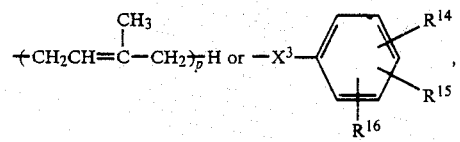

where p and X³ have the same meanings as defined hereinbefore and R¹⁴, R¹⁵ and R¹⁶ each represent a lower alkoxyl group and are present in the 2,3,4- or 3,4,5-positions of the benzene ring or a pharmacologically acceptable salt thereof.

4. The compound of claim 1, which is a 3,4-dihydrobenzopyran derivative of the formula $$\text{(I-23)}$$

wherein R¹, R², R³, R⁴, X² and n have the same meanings as defined hereinbefore; when X² is a methylene group, R⁶³ represents a lower alkyl group or a lower alkyl group substituted by a hydroxyl group, $$-\overset{O}{\underset{\|}{C}}-CH_2-(CH_2CH=\overset{CH_3}{\underset{|}{C}}-CH_2)_{\overline{q}}H \text{ or } -\overset{O}{\underset{\|}{C}}-\underset{R^{101}}{\overset{R^{71}}{\diagdown}}\overset{R^{81}}{\underset{R^{91}}{Q^1}}$$

and when X² is a carbonyl group, R⁶³ represents $$-CH_2-\underset{R^{102}}{\overset{R^{72}}{\diagdown}}\overset{R^{82}}{\underset{R^{92}}{Q^2}},$$

where g, R⁷¹, R⁸¹, R⁹¹, R¹⁰¹, Q¹, R⁷², R⁸², R⁸², R⁹², R¹⁰² and Q² have the same meanings as defined hereinbefore or a pharmacologically acceptable salt thereof.

5. The compound of claim 4, which is a 3,4-dihydrobenzopyran derivative of the formula $$\text{(I-24)}$$

wherein R⁷³, R⁸³ and R⁹³ each represent a hydrogen atom or a methoxy group; when all of R⁷³, R⁸³ and R⁹³ represent hydrogen atoms, either one of X² and X³ represent a methylene group with the other group being a carbonyl group, all or R¹², R³² and R⁴² represent hydrogen atoms and R²² represents a chlorine atom, or all of R¹², R³² and R⁴² represent methyl groups and R²² represents a methoxy group; or when R⁷³ and R⁸³ each represent a methoxy group, R⁹³ represents a hydrogen atom, X² represents a methylene group or a carbonyl group and X³ represents a methylene group, or when R⁷³ represents a hydrogen atom, R⁸³ and R⁹³ each represent a methoxy group, X² represents a methylene group and X³ represents a carbonyl group, all of R¹², R³² and R⁴² represent methyl groups and R²² represents a methoxy group or all of R¹², R²² and R⁴² represent hydrogen atoms and R³² represents a methoxy group; or a pharmacologically acceptable salt thereof.

6. The compound of claim 4, which is a 3,4-dihydrobenzopyran derivative of the formula $$\text{(I-25)}$$

wherein R⁶⁴ represents a lower alkyl group substituted by a hydroxyl group or a pharmacologically acceptable salt thereof.

7. The compound of claim 1 which is 3,4-dihydro-6-methoxy-2-[2-(piperazin-1-yl)ethyl]-2,5,7,8-tetramethyl-2H-benzopyran.

8. The compound of claim 1 which is 3,4-dihydro-6-methoxy-2-[2-[4-(3-methyl-2-butenyl)piperazin-1-yl]-ethyl]-2,5,7,8-tetramethyl-2H-benzopyran.

9. The compound of claim 1 which is 3,4-dihydro-6-methoxy-2-[2-[4-(3,7-dimethyl-2,6-octadienyl)piperazin-1-yl]ethyl]-2,5,7,8-tetramethyl-2H-benzopyran.

10. The compound of claim 1 which is 3,4-dihydro-6-methoxy-2-[2-[4-(3,7,11-trimethyl-2,6,10-dodecatrienyl)piperazin-1-yl]ethyl]-2,5,7,8-tetramethyl-2H-benzopyran.

11. The compound of claim 1 which is 3,4-dihydro-6-methoxy-2-[2-[4-(3,7,11,15-tetramethyl-2,6,10,14-hexadecatetraenyl)piperazin-1-yl]ethyl]-2,5,7,8-tetramethyl-2H-benzopyran.

12. The compound of claim 1 which is 3,4-dihydro-6-methoxy-2-[2-[4-(3,4,5-trimethoxybenzoyl)piperazin-1-yl]ethyl]-2,5,7,8-tetramethyl-2H-benzopyran.

13. The compound of claim 1 which is 3,4-dihydro-6-methoxy-2-[2-[4-(3,4,5-trimethoxybenzyl)piperazin-1-yl]ethyl]-2,5,7,8-tetramethyl-2H-benzopyran.

14. The compound of claim 1 which is 1-[2-(3,4-dihydro-6-methoxy-2,5,7,8-tetramethyl-2H-benzopyran-2-yl)ethyl]-4-(4-methoxybenzoyl)piperazine.

15. The compound of claim 1 which is 1-[2-(3,4-dihydro-6-methoxy-2,5,7,8-tetramethyl-2H-benzopyran-2-yl)ethyl]-4-(4-dimethylaminobenzoyl)piperazine.

16. The compound of claim 1 which is 1-[2-(3,4-dihydro-6-methoxy-2,5,7,8-tetramethyl-2H-benzopyran-2-yl)ethyl]-4-(4-nitrobenzoyl)piperazine.

17. The compound of claim 1 which is 1-[2-(3,4-dihydro-6-methoxy-2,5,7,8-tetramethyl-2H-benzopyran-2-yl)ethyl]-4-(4-bromobenzoyl)piperazine.

18. The compound of claim 1 which is 1-[2-(3,4-dihydro-6-methoxy-2,5,7,8-tetramethyl-2H-benzopyran-2-yl)ethyl]-4-(4-pyridylcarbonyl)piperazine.

19. The compound of claim 1 which is 1-[2-(3,4-dihydro-6-methoxy-2,5,7,8-tetramethyl-2H-benzopyran-2-yl)ethyl]-4-(5,9,13-trimethyl-4,8,12-tetradecatrienoyl)-piperazine.

20. The compound of claim 1 which is 1-[2-(3,4-dihydro-7-methoxy-2-methyl-2H-benzopyran-2-yl)ethyl]-4-(3,4,5-trimethoxybenzoyl)piperazine.

21. The compound of claim 1 which is 1-[2-(6-chloro-3,4-dihydro-2-methyl-2H-benzopyran-2-yl)ethyl]-4-(4-methoxybenzoyl)piperazine.

22. The compound of claim 1 which is 1-[3-(3,4-dihydro-6-methoxy-2,5,7,8-tetramethyl-2H-benzopyran-2-yl)propyl]-4-(4-methoxybenzoyl)piperazine.

23. The compound of claim 1 which is 1-[(3,4-dihydro-6-methoxy-2,5,7,8-tetramethyl-2H-benzopyran-2-yl)acetyl]-4-(2,3,4-trimethoxybenzyl)piperazine.

24. The compound of claim 1 which is 1-[(6-chloro-3,4-dihydro-2-methyl-2H-benzopyran-2-yl)acetyl]-4-(2,3,4-trimethoxybenzyl)piperazine.

25. The compound of claim 1 which is 1-[(3,4-dihydro-6-methoxy-2,5,7,8-tetramethyl-2H-benzopyran-2-yl)carbonyl]-4-(2,3,4-trimethoxybenzyl)piperazine.

26. The compound of claim 1 which is 1-[2-(3,4-dihydro-6-methoxy-2,5,7,8-tetramethyl-2H-benzopyran-2-yl)ethyl]-4-(2,3,4-trimethoxybenzyl)piperazine.

27. The compound of claim 1 which is 1-benzoyl-4-[2-(3,4-dihydro-6-methoxy-2,5,7,8-tetramethyl-2H-benzopyran-2-yl)ethyl]piperazine.

28. The compound of claim 1 which is 1-[2-(3,4-dihydro-6-methoxy-2,5,7,8-tetramethyl-2H-benzopyran-2-yl)ethyl]-4-methylpiperazine.

29. The compound of claim 1 which is 1-[2-(3,4-dihydro-6-methoxy-2,5,7,8-tetramethyl-2H-benzopyran-2-yl)ethyl]-4-isopentylpiperazine.

30. The compound of claim 1 which is 1-[2-(3,4-dihydro-6-methoxy-2,5,7,8-tetramethyl-2H-benzopyran-2-yl)ethyl]-4-(2-hydroxyethyl)piperazine.

31. The compound of claim 1 which is 1-[2-(3,4-dihydro-6-methoxy-2,5,7,8-tetramethyl-2H-benzopyran-2-yl)ethyl]-4-(3-hydroxypropyl)piperazine.

32. A pharmaceutical composition for the treatment of peptic ulcer, cough or sputum, said composition comprising an amount effective to treat peptic ulcer, cough or sputum of a 3,4-dihydrobenzopyran derivative of the formula

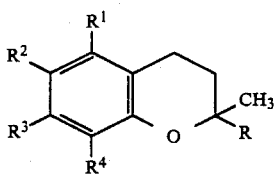
(I)

wherein $R^1$ and $R^4$ each represent a hydrogen atom or a lower alkyl group; $R^2$ represents a hydrogen atom, a halogen atom, a lower alkoxyl group or a lower alkenyloxy group; $R^3$ represents a hydrogen atom, a lower alkyl group or a lower alkoxyl group; R represents a group of the following formula (2)

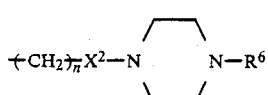
(2)

wherein n represents an integer of 0, 1 or 2; $X^2$ represents a methylene group or a carbonyl group; when $X^2$ represents a methylene group, $R^6$ represents a lower alkyl group or a lower alkyl group substituted by a hydroxyl group,

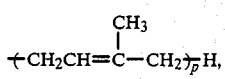

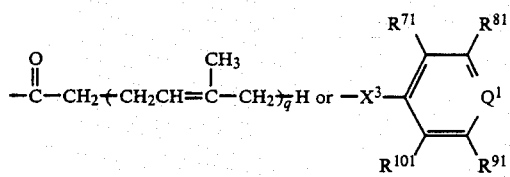

and when $X^2$ represents a carbonyl group, $R^6$ represents

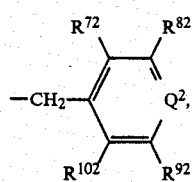

where p and q each represent an integer of 0 to 4; $X^3$ represents a methylene group or a carbonyl group; $Q^1$ represents a nitrogen atom (=N—), a carbon atom

where $R^{111}$ represents a hydrogen atom, a lower alkoxyl group, a halogen atom, a di-lower alkylamino group or a nitro group; $R^{71}$, $R^{81}$, $R^{91}$ and $R^{101}$ each represent a hydrogen atom or a lower alkoxyl group; $Q^2$ represents a nitrogen atom (=N—), a substituted carbon atom

where $R^{112}$ represents a hydrogen atom, a lower alkoxyl group, a halogen atom, a di-lower alkylamino group or a nitro group; and $R^{72}$, $R^{82}$, $R^{92}$ and $R^{102}$ each represent a hydrogen atom or a lower alkoxyl group; or a pharmacologically acceptable salt thereof and a pharmaceutically acceptable diluent or carrier.

33. A pharmaceutical composition for the treatment of peptic ulcer which comprises an effective amount to treat peptic ulcer of a 3,4-dihydrobenzopyran derivative of the formula

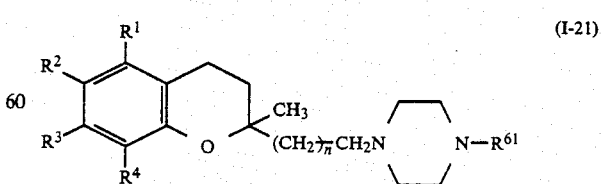
(I-21)

wherein $R^1$ and $R^4$ each represent a hydrogen atom or a lower alkyl group; $R^2$ represents a hydrogen atom, a halogen atom, a lower alkoxyl group or a lower alkenyloxy group; $R^3$ represents a hydrogen atom, a lower alkyl group or a lower alkoxyl group; n represents an integer of 0, 1 or 2; $R^{61}$ represents

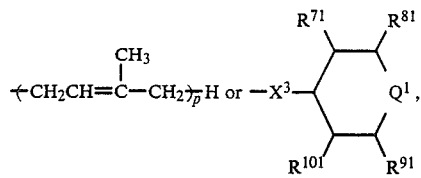

where p represents an integer of 0 to 4, $X^3$ represents a methylene group or a carbonyl group, $Q^1$ represents a nitrogen atom (=N—), a carbon atom

where $R^{111}$ represents a hydrogen atom, a lower alkoxyl group, a halogen atom, a di-lower alkylamino group or a nitro group; $R^{71}$, $R^{81}$, $R^{91}$ and $R^{101}$ each represent a hydrogen atom or a lower alkoxyl group; or a pharmacologically acceptable salt thereof and a pharmaceutically acceptable diluent or carrier.

34. A pharmaceutical composition useful as an antitussive and/or expectorant which comprises as an active ingredient an amount effective as an antitussive and/or expectorant of 3,4-dihydrobenzopyran derivative of the formula

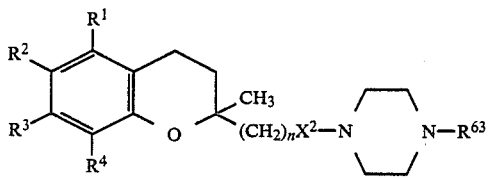

wherein $R^1$ and $R^4$ each represent a hydrogen atom or a lower alkyl group; $R^2$ represents a hydrogen atom, a halogen atom, a lower alkoxyl group or a lower alkenyloxy group; $R^3$ represents a hydrogen atom, a lower alkyl group or a lower alkoxyl group; n-represents an integer of 0, 1 or 2; $X^2$ represents a methylene group or a carbonyl group; when $X^2$ represents a methylene group, $R^{63}$ represents a lower alkyl group or a lower alkyl group substituted by a hydroxyl group,

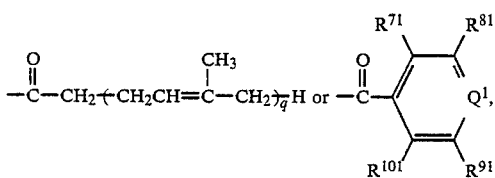

and when $X^2$ represents a carbonyl group, $R^{63}$ represents

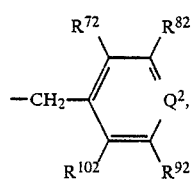

where q represents an integer of 0 to 4, $Q^1$ represents a nitrogen atom (=N—), a carbon atom

where $R^{111}$ represents a hydrogen atom, a lower alkoxyl group, a halogen atom, a di-lower alkylamino group or a nitro group; $R^{71}$, $R^{81}$, $R^{91}$ and $R^{101}$ each represent a hydrogen atom or a lower alkoxyl group; $Q^2$ represents a nitrogen atom (=N—), a carbon atom

where $R^{112}$ represents a hydrogen atom, a lower alkoxyl group, a halogen atom, a di-lower alkylamino group or a nitro group; $R^{72}$, $R^{82}$, $R^{92}$ and $R^{102}$ each represent a hydrogen atom or a lower alkoxyl group; or a pharmacologically acceptable salt thereof and a pharmaceutically acceptable diluent or carrier.

35. A method for treating peptic ulcer, cough or sputum, which comprises administering an effective amount to treat peptic ulcer, cough or sputum, of a 3,4-dihydrobenzopyran derivative of the formula

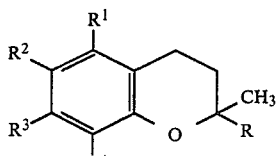

wherein $R^1$ and $R^4$ each represent a hydrogen atom or a lower alkyl group; $R^2$ represents a hydrogen atom, a halogen atom, a lower alkoxyl group or a lower alkenyloxy group; $R^3$ represents a hydrogen atom, a lower alkyl group or a lower alkoxyl group; R represents a group of the following formula (2)

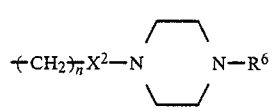

wherein n represents an integer of 0, 1 or 2; $X^2$ represents a methylene group or a carbonyl group; when $X^2$ represents a methylene group, $R^6$ represents a lower alkyl group or a lower alkyl group substituted by a hydroxyl group,

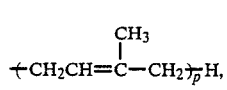

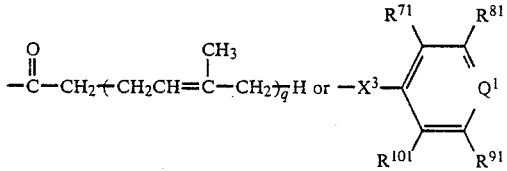

and when $X^2$ represents a carbonyl group, $R^6$ represents

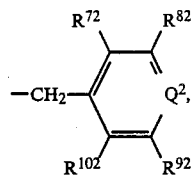

where p and q each represent an integer of 0 to 4; $X^3$ represents a methylene group or a carbonyl group; $Q^1$ represents a nitrogen atom (=N—), a carbon atom

where $R^{111}$ represents a hydrogen atom, a lower alkoxyl group, a halogen atom, a di-lower alkylamino group or a nitro group; $R^{71}$, $R^{81}$, $R^{91}$ and $R^{101}$ each represent a hydrogen atom or a lower alkoxyl group; $Q^2$ represents a nitrogen atom (=N—), a carbon atom

where $R^{112}$ represents a hydrogen atom, a lower alkoxyl group, a halogen atom, a di-lower alkylamino group or a nitro group; and $R^{72}$, $R^{82}$, $R^{92}$ and $R^{102}$ each represent a hydrogen atom or a lower alkoxyl group; or a pharmacologically acceptable salt thereof.

* * * * *